(12) United States Patent
Shea et al.

(10) Patent No.: US 8,597,640 B2
(45) Date of Patent: Dec. 3, 2013

(54) OVER-THE-COUNTER VITAMIN/NUTRICEUTICAL FORMULATION THAT PROVIDES NEUROPROTECTION AND MAINTAINS OR IMPROVES COGNITIVE PERFORMANCE IN ALZHEIMER'S DISEASE AND NORMAL AGING

(75) Inventors: Thomas B. Shea, Billerica, MA (US); Amy Y. Chan-Daniels, Tewksbury, MA (US)

(73) Assignee: University of Massachusetts Lowell, Lowell, MA (US)

(*) Notice: Subject to any disclaimer, the term of this patent is extended or adjusted under 35 U.S.C. 154(b) by 1425 days.

(21) Appl. No.: 12/080,756

(22) Filed: Apr. 4, 2008

(65) Prior Publication Data
US 2009/0110745 A1 Apr. 30, 2009

Related U.S. Application Data

(60) Provisional application No. 61/001,149, filed on Oct. 31, 2007.

(51) Int. Cl.
*A61K 38/43* (2006.01)
*A01N 61/00* (2006.01)

(52) U.S. Cl.
USPC ............ 424/94.1; 514/1; 514/52; 514/458; 514/579

(58) Field of Classification Search
None
See application file for complete search history.

(56) References Cited

U.S. PATENT DOCUMENTS

| | | | |
|---|---|---|---|
| 3,810,994 A | 5/1974 | Wiegand | |
| 4,255,449 A | 3/1981 | Cavazza | |
| 4,268,524 A | 5/1981 | Cavazza | |
| 4,751,242 A | 6/1988 | Calvani et al. | |
| 4,940,658 A | 7/1990 | Allen et al. | |
| 4,945,083 A | 7/1990 | Jansen, Jr. | |
| 4,968,719 A | 11/1990 | Brevetti | |
| 5,043,355 A | 8/1991 | Cavazza | |
| 5,192,805 A | 3/1993 | Cavazza | |
| 5,364,845 A | 11/1994 | Henderson | |
| 5,563,126 A | 10/1996 | Allen et al. | |
| 5,587,363 A | 12/1996 | Henderson | |
| 5,753,703 A | 5/1998 | Cavazza et al. | |
| 5,795,873 A | 8/1998 | Allen | |
| 5,916,912 A | 6/1999 | Ames et al. | |
| 5,958,886 A | 9/1999 | Carter et al. | |
| 5,997,915 A | 12/1999 | Bailey et al. | |
| 6,008,221 A | 12/1999 | Smith et al. | |
| 6,011,040 A | 1/2000 | Muller et al. | |
| 6,020,139 A | 2/2000 | Schwartz et al. | |
| 6,037,373 A | 3/2000 | De Simone | |
| 6,080,788 A | 6/2000 | Sole et al. | |
| 6,207,651 B1 | 3/2001 | Allen et al. | |
| 6,254,904 B1 | 7/2001 | Bailey | |
| 6,297,224 B1 | 10/2001 | Allen et al. | |
| 6,335,021 B1 | 1/2002 | Cavazza | |
| 6,335,361 B1 | 1/2002 | Hamilton | |
| 6,368,617 B1 | 4/2002 | Hastings et al. | |
| 6,369,058 B1 | 4/2002 | Hussain et al. | |
| 6,479,069 B1 | 11/2002 | Hamilton | |
| 6,528,496 B1 | 3/2003 | Allen et al. | |
| 6,544,547 B2 | 4/2003 | Hageman | |
| 6,562,869 B1 | 5/2003 | Hamilton et al. | |
| 6,565,876 B1 | 5/2003 | Cavazza | |
| 6,589,555 B2 | 7/2003 | Pandya | |
| 6,596,701 B1 | 7/2003 | Schwartz et al. | |
| 6,673,837 B2 | 1/2004 | Fassi | |
| 6,712,802 B1 | 3/2004 | Cairns et al. | |
| 6,733,797 B1 | 5/2004 | Summers | |
| 6,746,678 B1 | 6/2004 | Shapiro | |
| 6,784,209 B1 | 8/2004 | Gardiner et al. | |
| 6,822,002 B1 | 11/2004 | Arduini | |
| 6,964,969 B2 | 11/2005 | McCleary | |
| 7,049,321 B2 | 5/2006 | Fisher et al. | |
| 7,211,571 B2 | 5/2007 | Pola | |
| 2003/0119904 A1 | 6/2003 | Fassi | |
| 2004/0152760 A1* | 8/2004 | Castillo et al. | 514/453 |
| 2005/0043312 A1 | 2/2005 | Shea et al. | |
| 2005/0107338 A1 | 5/2005 | Seidman | |
| 2006/0004095 A1 | 1/2006 | Calvani et al. | |
| 2006/0088574 A1* | 4/2006 | Manning et al. | 424/439 |
| 2006/0127506 A1* | 6/2006 | Hebert | 424/730 |
| 2006/0134147 A1 | 6/2006 | Kalafsky | |
| 2007/0213408 A1 | 9/2007 | Calvani et al. | |

FOREIGN PATENT DOCUMENTS

| | | |
|---|---|---|
| CA | 2291959 | 6/2001 |
| DE | 19824346 A1 | 12/1999 |
| EP | 0516594 A1 | 12/1992 |
| EP | 0808626 A1 | 11/1997 |
| WO | 02/32434 A1 | 4/2002 |

OTHER PUBLICATIONS

American Institute of Nutrition AIN-76 Semipurified Diet [online] Mar. 20, 1980 [retrieved on Sep. 20, 2011] retrieved from http://www4.mpbio.com/ecom/docs/proddata.nsf/(webtds2)/960357.*
Lowell Sun search results [online] [retrieved on Sep. 21, 2011] retrieved from http://nl.newsbank.com.*
Scrimenti, B. UML Markets Memory Booster. Lowell Sun, Aug. 23, 2009.*
Wolters et al. "Cobalamin: a critical vitamin in the elderly." Preventive Medicine 39:1256-1266 (2004).*
Hatherill, J. The Brain Gate. LifeLine Press (2003). Cover, front matter and pp. 151-153.*

(Continued)

*Primary Examiner* — Samuel Woolwine

(74) *Attorney, Agent, or Firm* — Nelson Mullins Riley & Scarborough LLP; Debra J. Milasincic, Esq.; Briana M. Erickson

(57) ABSTRACT

The present invention provides methods for improving cognitive function, improving mood, and decreasing aggression in a normal adult subject, and in a subject having symptoms characteristic of a neurological disorder, by administration of a nutriceutical formulation of the invention to the subject. The invention additionally features methods of treating neurological disorders, depression, and aggression using nutriceutical formulations. Nutriceutical compositions and formulations for use in the methods of the invention, and kits containing nutriceutical compositions and formulations, are also provided.

17 Claims, 20 Drawing Sheets

(56) References Cited

OTHER PUBLICATIONS

Ogden et al. Mean Body Weight, Height, and Body Mass Index, United States 1960-2002. Advance Data From Vital and Health Statistics, No. 347, Oct. 27, 2004 (pp. 1-17 and 20).*

Blom, Henk J., "Consequences of Homocysteine Export and Oxidation in the Vascular System," Seminars in Thrombosis and Hemostasis, vol. 26(3):227-232 (2000).

Bottiglieri, T. et al., "Cerebrospinal fluid S-adenosylmethionine in depression and dementia: effects of treatment with parenteral and oral S-adenosylmethionine," J. Neurol. Neurosurg. Psychiatry, vol. 53(12):1096-1098 (1990).

Bottiglieri, T. et al., "S-adenosylmethionine levels in psychiatric and neurological disorders: a review," Acta Neurol. Scand., vol. 154(Suppl.):19-26 (1994).

Bottiglieri, Teodoro et al., "The Clinical Potential of Ademetionine (S-Adenosylmethionine) in Neurological Disorders," Drugs, vol. 48(2):137-152 (1994).

Bretsky, P.M. et al., "Evidence for the Interaction between Apolipoprotein E Genotype, Gender, and Alzheimer Disease," Alzheimer Disease and Associated Disorders, vol. 13(4):216-221 (1999).

Brooks, John O. III et al., "Acetyl L-Carnitine Slows Decline in Younger Patients With Alzheimer's Disease: A Reanalysis of the Double-Blind, Placebo-Controlled Study Using the Trilinear Approach," International Psychogeriatrics, vol. 10(2):193-203 (1998).

Chan, Amy et al., "Folate deprivation increases presenilin expression, gamma-secretase activity, and Abeta levels in murine brain: potentiation by ApoE deficiency and alleviation by dietary S-adenosyl methionine," Journal of Neurochemistry, vol. 102:753-760 (2007).

Chiang, Peter K. et al., "S-Adenosyl-L-homocysteine Hydrolase: Analogues of S-Adenosyl-L-homocysteine as Potential Inhibitors," Molecular Pharmacology, vol. 13:939-947 (1977).

Christensen, Benedicte et al., "Homocysteine Export From Cells Cultured in the Presence of Physiological and Superfluous Levels of Methionine: Methionine Loading of Non-Transformed, Transformed, Proliferating, and Quiescent Cells in Culture," Journal of Cellular Physiology, vol. 146:52-62 (1991).

Cloughesy, Timothy F. et al., "Pharmacological blood-brain barrier modification for selective drug delivery," Journal of Neuro-Oncology, vol. 26:125-132 (1995).

Dringen, Ralf et al., "N-Acetylcysteine, but not methionine or 2-oxothiazolidine-4-carboxylate, serves as cysteine donor for the synthesis of glutathione in cultured neurons derived from embryonal rat brain," Neuroscience Letters, vol. 259:79-82 (1999).

Ekinci, Fatma J. et al., "Beta-Amyloid-induced calcium influx induces apoptosis in culture by oxidative stress rather than tau phosphorylation," Molecular Brain Research, vol. 389-395 (2000).

Ekinci, Fatma J. et al., "Beta-Amyloid-Induced Tau Phosphorylation does not Correlate with Degeneration in Cultured Neurons," Journal of Alzheimer's Disease, vol. 2:7-15 (2000).

Endresen, Petter C. et al., "Apoptosis and Transmethylation Metabolites in HL-60 Cells," The Journal of Pharmacology and Experimental Therapeutics, vol. 278(3):1318-1324 (1996).

Fiskerstrand, Torunn et al., "Folate Depletion Induced by Methotrexate Affects Methionine Synthase Activity and Its Susceptibility to Inactivation by Nitrous Oxide," The Journal of Pharmacology and Experimental Therapeutics, vol. 282(3):1305-1311 (1997).

Grundman, Michael, "Vitamin E and Alzheimer disease: the basis for additional clinical trials," Am. J. Clin. Nutr., vol. 71(Suppl.):630S-636S (2000).

Hatanaka, Yutaka et al., "A Role of Peroxides in Ca2+ ionophore-Induced Apoptosis in Cultured Rat Cortical Neurons," Biochemical and Biophysical Research Communications, vol. 227:513-518 (1996).

Ho, Pei I. et al., "Folate deprivation induces neurodegeneration: roles of oxidative stress and increased homocysteine," Neurobiology of Disease, vol. 14:32-42 (2003).

Holcomb, Leigh A. et al., "Behavioral Changes in Transgenic Mice Expressing Both Amyloid Precursor Protein and Presenilin-1 Mutations: Lack of Association with Amyloid Deposits," Behavior Genetics, vol. 29(3):177-185 (1999).

Huang, G. Steven et al., "Differential gene expression of livers from ApoE deficient mice," Life Sciences, vol. 19-28 (2000).

Jeong, Seong-Yun et al., "3-Deazaadenosine, a S-Adenosylhomocysteine Hydrolase Inhibitor, Has Dual Effects on NF-kB Regulation," The Journal of Biological Chemistry, vol. 274(27):18981-18988 (1999).

Kennedy, B.P. et al., "Elevated S-adenosylhomocysteine in Alzheimer brain: influence on methyltransferases and cognitive function," Journal of Neural Transmission, vol. 111:547-567 (2004).

Lovell, M.A. et al., "Decreased glutathione transferase activity in brain and ventricular fluid in Alzheimer's disease," Neurology, vol. 51:1562-1566 (1998).

Lucock, M.D. et al., "The Influence of Dietary Folate and Methionine on the Metabolic Disposition of Endotoxic Homocysteine," Biochemical and Molecular Medicine, vol. 59:104-111 (1996).

Mattson, Mark P. et al., "Folate and homocysteine metabolism in neural plasticity and neurodegenerative disorders," Trends in Neurosciences, vol. 26(3):137-146 (2003).

Mischoulon, David et al., "Role of S-adenosyl-L-methionine in the treatment of depression: a review of the evidence," Am. J. Clin. Nutr., vol. 76(Suppl.):1158S-1161S (2002).

Olivieri, G. et al., "N-Acetyl-L-cysteine protects SHSY5Y neuroblastoma cells from oxidative stress and cell cytotoxicity: effects on beta-amyloid secretion and tau phosphorylation," Journal of Neurochemistry, vol. 76:224-233 (2001).

Ou, Ying C. et al., "The Role of Intracellular Glutathione in Methylmercury-Induced Toxicity in EMbryonic Neuronal Cells," NeuroToxicology, vol. 20(5):793-804 (1999).

Parihar, M.S. et al., "Alzheimer's disease pathogenesis and therapeutic interventions," Journal of Clinical Neuroscience, vol. 11(5):456-467 (2004).

Ramassamy, Charles et al., "Impact of apoE deficiency on oxidative insults and antioxidant levels in the brain," Molecular Brain Research, vol. 86:73-83 (2001).

Ramassamy, Charles et al., "Oxidative Damage and Protection by Antioxidants in the Frontal Cortex of Alzheimer's Disease is Related to the Apolipoprotein E Genotype," Free Radical Biology & Medicine, vol. 27(5/6):544-553 (1999).

Rimon, Galia et al., "Increased Surface Phosphatidylserine Is an Early Marker of Neuronal Apoptosis," Journal of Neuroscience Research, vol. 48:563-570 (1997).

Scorziello, A. et al., "Acetyl-L-Carnitine Arginine Amide Prevents beta 25-35-Induced Neurotoxicity in Cerebellar Granule Cells," Neurochemical Research, vol. 22(3):257-265 (1997).

Shea, Thomas B. et al., "Apolipoprotein E Deficiency Promotes Increased Oxidative Stress and Compensatory Increases in Antioxidants in Brain Tissue," Free Radical Biology & Medicine, vol. 33(8):1115-1120 (2002).

Shea, Thomas B. et al., "Efficacy of Vitamin E, Phosphatidyl Choline, and Pyruvate on Buffering Neuronal Degeneration and Oxidative Stress in Cultured Cortical Neurons and in Central Nervous Tissue of Apolipoprotein E-Deficient Mice," Free Radical Biology & Medicine, vol. 33(2):276-282 (2002).

Shea, Thomas B., "Effects of Dietary Supplementation with N-Acetyl Cysteine, Acetyl-L-Carnitine and S-Adenosyl Methionine on Cognitive Performance and Aggression in Normal Mice and Mice Expressing Human ApoE4," Neuromol. Med., vol. 9:264-269 (2007).

Shea, Thomas B. et al., "Folate quenches oxidative damage in brains of apolipoprotein E-deficient mice: augmentation by vitamin E," Molecular Brain Research, vol. 108:1-6 (2002).

Shulz, Jorg B. et al., "Glutathione, oxidative stress and neurodegeneration," Eur. J. Biochem., vol. 267:4904-4911 (2000).

Tapiero, H. et al., "Prevention of pathologies associated with oxidative stress and dietary intake deficiencies: folate deficiency and requirements," Biomed. Pharmacother., vol. 55:381-390 (2001).

(56) References Cited

OTHER PUBLICATIONS

Tchantchou, Flaubert et al., "Increased Transcription and Activity of Glutathione Synthase in Response to Deficiencies in Folate, Vitamen E, and Apolipoprotein E," Journal of Neuroscience Research, vol. 75:508-515 (2004).

Thal, L.J. et al., "A 1-year controlled trial of acetyl-L-carnitine in early-onset AD," Neurology, vol. 55:805-810 (2000).

Trolin, Cecilia Gomes et al., "Brain ATP: L-methionine S-adenosyltransferase (MAT), S-adenosylmethionine (SAM) and S-adenosylhomocysteine (SAH): regional distribution and age-related changes," European Neuropsychopharmacology, vol. 4:469-477 (1994).

Yang, Xiaoda et al., "Mechanisms of Inactivation of Human S-Adenosylhomocysteine Hydrolase by 5',5',6',6'-Tetradehydro-6'-deoxy-6'-halohomoadenosines," Biochemistry, vol. 39:15234-15241 (2000).

Chan, Amy et al., "A Novel Vitamin/Nutraceutical Formulation that Delays Cognitive Decline and Improves Mood in Early-Stage Alzheimer's Disease," Alzheimer's Diseae, vol. 3:S98, Abstract No. P-011 (2007).

Chan, Amy et al., "Apple juice concentrate maintains acetylcholine levels following dietary compromise," Journal of Alzheimer's Disease, vol. 9:287-291 (2006).

Chan, Amy et al., "A Vitamin/Nutriceutical Formulation Improves Memory and Cognitive Performance in Community-Dwelling Adults Without Dementia," J. Nutr. Health Aging, vol. 14(3):224-230 (2010).

Chan, Amy, "Can Dietary Supplements Prevent Cognitive Decline Observed in Aging and Alzheimer's Disease?" University of Massachusetts, Lowell, Dissertation Publication No. 3242266 (2007).

Chan, Amy et al., "Dietary and Genetic Compromise in Folate Availability Reduces Acetylcholine, Cognitive Performance and Increases Aggression: Critical Role of S-Adenosyl Methionine," The Journal of Nutrition, Heath & Aging, vol. 12(4):252-261 (2008).

Chan, Amy et al., "Dietary and genetically-induced oxidative stress alter tau phosphorylation: Influence of folate and apolipoprotein E deficiency," Journal of Alzheimer's Disease, vol. 9:399-405 (2006).

Chan, Amy et al., "Efficacy of a Vitamin/Nutriceutical Formulation for Early-stage Alzheimer's Disease: A 1-year, Open-label Pilot Study With a 16-Month Caregiver Extension," American Journal of Alzheimer's Disease & Other Dementias, vol. 23(6):571-585 (2009).

Chan, Amy et al., "Supplementation with apple juice attenuates presenilin-1 overexpression during dietary and genetically-induced oxidative stress," Journal of Alzheimer's Disease, vol. 10:353-358 (2006).

Dawn-Linsley, Maria et al., "Monitoring thiobarbituric acid-reactive substances (TBARs) as an assay for oxidative damage in neuronal cultures and central nervous system," Journal of Neuroscience Methods, vol. 141:219-222 (2005).

Dhitavat, Sirakarnt et al., "Acetyl-L-Carnitine Protects against Amyloid-Beta Neurotoxicity: Roles of Oxidative Buffering and ATP Levels," Neurochemical Research, vol. 27(6):501-505 (2002).

Dhitavat, Sirakarnt et al., "Differential efficacy of lipophilic and cytosolic antioxidants on generation of reactive oxygen species by amyloid-b," Journal of Alzheimer's Disease, vol. 3:525-529 (2001).

Dhitavat, Sirikarnt et al., "Folate, vitamin E, and acetyl-L-carnitine provide synergistic protection against oxidative stress resulting from exposure of human neuroblastoma cells to amyloid-beta," Brain Research, vol. 1061:114-117 (2005).

Dubey, Maya et al., "Potentiation of arsenic neurotoxicity by folate deprivation: Protective role of S-adenosyl methionine," Nutritional Neuroscience, vol. 10(5/6):199-204 (2007).

Ho, Pei I. et al., "Homocysteine potentiates beta-amyloid neurotoxicity: role of oxidative stress," Journal of Neurochemistry, vol. 78:1-6 (2001).

Ho, Pei I. et al., "Multiple Aspects of Homocysteine Neurotoxicity: Glutamate Excitotoxicity, Kinase Hyperactivation and DNA Damage," Journal of Neuroscience Research, vol. 70:694-702 (2002).

J.R., "A smart pill for seniors?" Science, vol. 171:301 (2007).

Lepore, Alicia et al., "Cognitive performance in normal seniors is enhanced by a nutraceutical formulation," The FASEB Journal, vol. 21:837.7 (2007).

Mihalick, Sheila M. et al., "Folate and Vitamin E Deficiency Impair Cogniti ve Performance in Mice Subjected to Oxidative Stress," NeuroMolecular Medicine, vol. 4:197-202 (2003).

Ortiz, Daniela et al., "Apple juice prevents oxidative stress induced by amyloid-beta in culture," Journal of Alzheimer's Disease, vol. 6:27-30 (2004).

Remington, Ruth et al., "Efficacy of a Vitamin/Nutriceutical Formulation for Moderate-stage to Later-stage Alzheimer's disease: A Placebo-controlled Pilot Study," American Journal of Alzheimer's Disease & Other Dementias, vol. 24(1):27-33 (2009).

Rogers, E.J. et al., "Apple Juice Prevents Oxidative Stress and Impaired Cognitive Performance Caused by Genetic and Dietary Deficiencies in Mice," The Journal of Nutrition & Aging, vol. 7(6):1-6 (2003).

Shea, Thomas B. et al., "17 beta-Estradiol alleviates synergistic oxidative stress resulting from folate deprivation and amyloid-beta treatment," Journal of Alzheimer's Disease, vol. 5:323-327 (2003).

Shea, Thomas B. et al., "Differential susceptibity of transgenic mice lacking one or both apolipoprotein alleles to folate and vitamin E deprivation," Journal of Alzheimer's Disease, vol. 4:1-5 (2002).

Shea, Thomas B., "Effects of Dietary Supplementation wtih N-Acetyl Cysteine, Acetyl-L-Carnitine and S-Adenosyl Methionine on Cognitive Performance and Aggression in Normal Mice and Mice Expressing Human ApoE4," Neuromol. Med., vol. 9:264-269 (2007).

Shea, T.B. et al., "Efficacy of Vitamin E, Phosphatidyl Choline and Pyruvate on Abeta Neurotoxicity in Culture," The Journal of Nutrition, Health & Aging, vol. 7(4):252-255 (2003).

Shea, Thomas B., "Folate, the methionine cycle, and Alzheimer's disease," Journal of Alzheimer's Disease, vol. 9:359-360 (2006).

Shea, Thomas B. et al., "Homocysteine and Dementia," N. Engl. J. Med., vol. 364(25):2007 (2002).

Shea, Thomas B. et al., "Homocysteine, folate deprivation and Alzheimer neuropathology," Journal of Alzheimer's Disease, vol. 4:261-267 (2002).

Shea, Thomas B. et al., "Nanosphere-mediated delivery of vitamen E increases its efficacy against oxidative stress resulting from exposure to amyloid beta," Journal of Alzheimer's Disease, vol. 7:297-301 (2005).

Shea, Thomas B. et al., "The S-Adenosyl Homocysteine Hydrolase Inhibitor 3-Deaza-Adenosine Prevents Oxidative Damage and Cognitive Impairment Following Folate and Vitamin E Deprivation in a Murine Model of Age-Related, Oxidative Stress-Induced Neurodegeneration," NeuroMolecular Medicine, vol. 5:173-182 (2004).

Shea, Thomas B. et al., "Vitamin E deficiency does not induce compensatory antioxidant increases in central nervous system tissue of apolipoprotein E-deficient mice," Journal of Alzheimer's Disease, vol. 5:9-14 (2003).

Tchantchou, Floubert et al., "Apple juice concentrate prevents oxidative damage and impaired maze performance in aged mice," Journal of Alzheimer's Disease, vol. 8:283-287 (2005).

Tchantchou, F. et al., "Dietary Supplementation with Apple Juice Concentrate Alleviates the Compensatory Increase in Glutathione Synthase Transcription and Activity that Accompanies Dietary- and Genetically-Induced Oxidative Stress," The Journal of Nutrition, vol. 8(6):492-496 (2004).

Tchantchou, Floubert et al., "Dietary Supplementation With 3-Deaza Adenosine, N-Acetyl Cysteine, and S-Adenosyl Methionine Provide Neuroprotection Against Multiple Consequences of Vitamin Deficiency and Oxidative Challenge," NeuroMolecular Medicine, vol. 6:93-104 (2004).

Tchantchou, Floubert et al., "Expression and activity of methionine cycle genes are altered following folate and vitamin E deficiency under oxidative challenge: Modulation by apolipoprotein E-deficiency," Nutritional Neuroscience, vol. 9(1/2):17-24 (2006).

(56) References Cited

OTHER PUBLICATIONS

Tchantchou, Floubert et al., "N-acteyl cysteine alleviates oxidative damage to central nervous system of ApoE-deficient mice following folate and vitamin E-deficiency," Journal of Alzheimer's Disease, vol. 7:135-138 (2005).

Tchantchou, F. et al., "S-Adenosyl Methionine: A Connection Between Nutritional and Genetic Risk Factors for Neurodegeneration in Alzheimer's Disease," The Journal of Nutritio, Health & Aging, vol. 10(6):541-544 (2006).

Tchantchou, Flaubert et al., "S-Adenosylmethionine Mediates Glutathione Efficacy by Increasing Glutathione S-Transferase Activity: Implications for S-Adenosyl Methionine as a Neuroprotective Dietary Supplement," Journal of Alzheimer's Disease, vol. 14:323-328 (2008).

Tjiattas, Lindsay et al., "Folate deficiency and homocysteine induce toxicity in cultured dorsal root ganglion neurons via cytosolic calcium accumulation," Aging Cell, vol. 3:71-76 (2004).

* cited by examiner

OVER-THE-COUNTER VITAMIN/NUTRICEUTICAL FORMULATION THAT PROVIDES NEUROPROTECTION AND MAINTAINS OR IMPROVES COGNITIVE PERFORMANCE IN ALZHEIMER'S DISEASE AND NORMAL AGING

RELATED APPLICATIONS

This patent application claims the benefit of U.S. Provisional Patent Application Ser. No. 61/001,149, entitled "An Over-the-Counter Vitamin/Nutriceutical Formulation that Provides Neuroprotection and Maintains or Improves Cognitive Performance in Alzheimer's Disease and Normal Aging" filed Oct. 31, 2007, the entire contents of which are incorporated herein by reference.

BACKGROUND OF THE INVENTION

Alzheimer's disease (AD), also known simply as Alzheimer's, is a neurodegenerative disease that, in its most common form, is found in people over age 65. Approximately 24 million people worldwide have dementia, of which the majority (~60%) is due to Alzheimer's (Ferri C. P. et al. (2005) Lancet 366(9503):2112-2117). More than 5 million Americans are estimated to have Alzheimer's disease, and it is projected that this number will increase to 14.3 million by mid-century, representing a 350 percent increase from 2000.

The ultimate cause of Alzheimer's is unknown. Characteristic clinical symptoms of Alzheimer's disease include progressive cognitive deterioration, declining ability to participate in daily activities, neuropsychiatric symptoms, and behavioral changes. Plaques containing misfolded proteins, called beta amyloids, form in the brain many years before the clinical signs of Alzheimer's are observed. Together, these plaques and neurofibrillary tangles form the pathological hallmarks of the disease. These features can only be discovered at autopsy and help to confirm the clinical diagnosis.

The first readily identifiable symptoms of Alzheimer's disease are usually short-term memory loss and visual-spatial confusion. These initial symptoms progress from seemingly simple and often fluctuating forgetfulness and difficulty orienting oneself, to a more pervasive loss of short-term memory and difficulty navigating through familiar areas such as one's neighborhood, and ultimately progressing to loss of recognition of objects and persons. Aphasia, disorientation, and disinhibition often accompany the loss of memory. In later stages of the disease patients experience deterioration of musculature and mobility, leading to bedfastness, inability to feed oneself, and incontinence. While the onset, advancement, and severity of these conditions are highly variable in nature, the types of symptoms are common, including behavioral changes (e.g. depression and agitation), and loss of the ability to carry out basic daily activities (e.g. grooming, dressing, walking, etc.).

There is currently no cure for Alzheimer's disease. Current pharmacological treatments for mild to moderate AD include selective acetylcholinesterase inhibitors, such as Donepezil, and uncompetitive NMDA receptor antagonists, such as Memantine (Reisberg 2006, Feldman 2004). Clinical studies of these treatments have demonstrated efficacy relative to their mean rate of decline with a placebo (Johannsen 2006); however, in addition to a host of adverse events that accompany these treatments, there still remains a steady decline in performance on neuropsychological exams and caregiver's assessments over the course of these studies. Moreover, the average monthly costs of these treatments can exceed $1000 (Plosker 2005, Feldman 2004). At over $100 billion per year, AD is the third most costly disease in the U.S., after heart disease and cancer. There is therefore a current and growing need for an inexpensive, over-the-counter formulation that can improve symptoms commonly associated with Alzheimer's disease.

Behavioral and psychological symptoms of dementia (BPSD) often accompany Alzheimer's Disease, and generally worsen as the illness advances. The presence of non-cognitive behavioral symptoms such as mood disorders, psychosis, and aggressive behavior, can be equally or more taxing to caregivers as cognitive decline, and is often a deciding factor in the decision to institutionalize a patient. Aggressive behavior has been correlated with genetic risk factors, particularly the presence of the E4 allele of ApoE, known to confer considerable risk for onset and rapid progression of AD. Mice expressing the human ApoE4 allele have served as a useful animal model of AD. Cholinergic deficits have been linked to both cognitive decline and BPSD, in part by exacerbating vulnerability to the effects of other neurochemical imbalances. The highest level of cholinergic innervation is received by the limbic system, an area of the cortex affiliated with BPSD. Treatments for behavioral symptoms have traditionally included antipsychotic medications and benzodiazepines. These medications are, however, prescribed with caution due to the increased susceptibility of the elderly to a host of adverse side effects. Alternative treatments that are effective in treating the behavioral symptoms of AD are therefore highly desirable.

Poor nutrition has been shown to accelerate many symptoms associated with AD. For example, folate deficiency increases neuronal oxidative stress, in part by increasing levels of the neurotoxin homocysteine, which is related to the progression and severity of AD. Studies described herein demonstrate that folate deprivation potentiates at least 7 additional risk factors for AD; these include potentiation of genetic risk factors (presenilin-1 (PS-1) and ApoE deficiency), increased generation of the neurotoxic peptide amyloid-Beta and increased activity of the enzyme responsible for its generation (gamma secretase), an increase in hyperphosphorylation of tau (the precursor of neurofibrillary tangles) and a decline in the neurotransmitter acetylcholine, leading to impaired cognitive performance and increased aggression. As such, the development of a nutriceutical formulation that improves symptoms and slows the progression of AD would provide a safe and cost-effective addition to current therapeutic strategies used to manage AD.

Given that AD is the most common form of dementia to afflict our rapidly aging society, there is a drive to not only treat patients diagnosed with AD, but also to initiate preventative measures to slow or prevent the onset of the disease (Mattson 2004, Post 1999). While attention has recently been given to pre-symptomatic AD detection, this attention has been devoted to defining and targeting the high-risk population. Although this is a logical approach, preventative measures for all aging individuals should be made, as the elderly is the fastest growing segment of the population. A nutriceutical formulation that is beneficial for patients with AD may additionally be useful as a preventative measure, and would be safe for administration to normal adults. Such a nutriceutical formulation may also be valuable for normal adults unaffected by AD who are nonetheless seeking to improve cognitive performance, improve mood, reduce depression, and reduce aggression.

SUMMARY OF THE INVENTION

The present invention is based, at least in part, on the discovery of novel nutriceutical formulations which improve cognitive function in normal adults. The formulations of the invention have been further shown to improve cognition in adults diagnosed with neurodegenerative disease, e.g., early-stage and mid/late-stage Alzheimer's Disease. In patients diagnosed with neurodegenerative disease, the formulations of the invention have additionally been shown to improve mood and behavior, reduce depression, and decrease aggression. The novel formulations include a combination of six vitamins, antioxidants and nutriceuticals that synergistically provide protection to brain cells. The fundamental components of the formulations of the invention are folic acid, vitamin B12, vitamin E, S-adenosyl methionine, N-acetyl cysteine, and acetyl-L-carnitine. These formulations are proposed to buffer neurons from oxidative attack or metabolic deficiencies, provide neurons with additional energy, aid neurons in utilization of antioxidants, and maintain neurotransmitter production. Accordingly, the formulations of the invention provide a novel therapeutic approach for improving cognition, mood, and behavior, and for reducing depression and aggression, in normal adults and in adults diagnosed with neurodegenerative disease.

Based at least in part on the above observations, the invention features, in a first aspect, methods of improving cognitive performance in a subject, comprising administering to the subject a nutriceutical formulation or composition of the invention. In another aspect, the invention features methods of reducing aggression in a subject, comprising administering to the subject a nutriceutical formulation or composition of the invention. In an additional aspect, the invention features methods of improving mood in a subject, comprising administering to the subject a nutriceutical formulation or composition of the invention. In one embodiment of these aspects, the subject is a normal adult. In another embodiment, the subject has been diagnosed with a neurodegenerative disorder. In an exemplary embodiment, the subject has been diagnosed with Alzheimer's Disease. In a related aspect, the invention features methods of treating a neurodegenerative disorder in a subject, comprising administering a therapeutically effective amount of a formulation or composition of the invention to the subject such that the disorder is treated. In an exemplary embodiment, the neurodegenerative disorder is Alzheimer's Disease.

The invention further features compositions comprising folate, vitamin E, vitamin B12, N-acetyl cysteine, acetyl-L-carnitine, and S-adenosyl methionine. In another aspect the invention features kits containing a nutriceutical formulation or composition of the invention together with instructions for administration to a subject. In a related aspect, the invention features kits containing a nutriceutical formulation or composition of the invention together with one or more additional nutriceuticals and instructions for administration. In another aspect, the invention features kits containing a nutriceutical formulation or composition of the invention together with a selection of cognitive exercises including sudoku puzzles and/or crossword puzzles.

Other features and advantages of the invention will be apparent from the following detailed description, and from the claims.

DETAILED DESCRIPTION OF THE INVENTION

Figure 1:
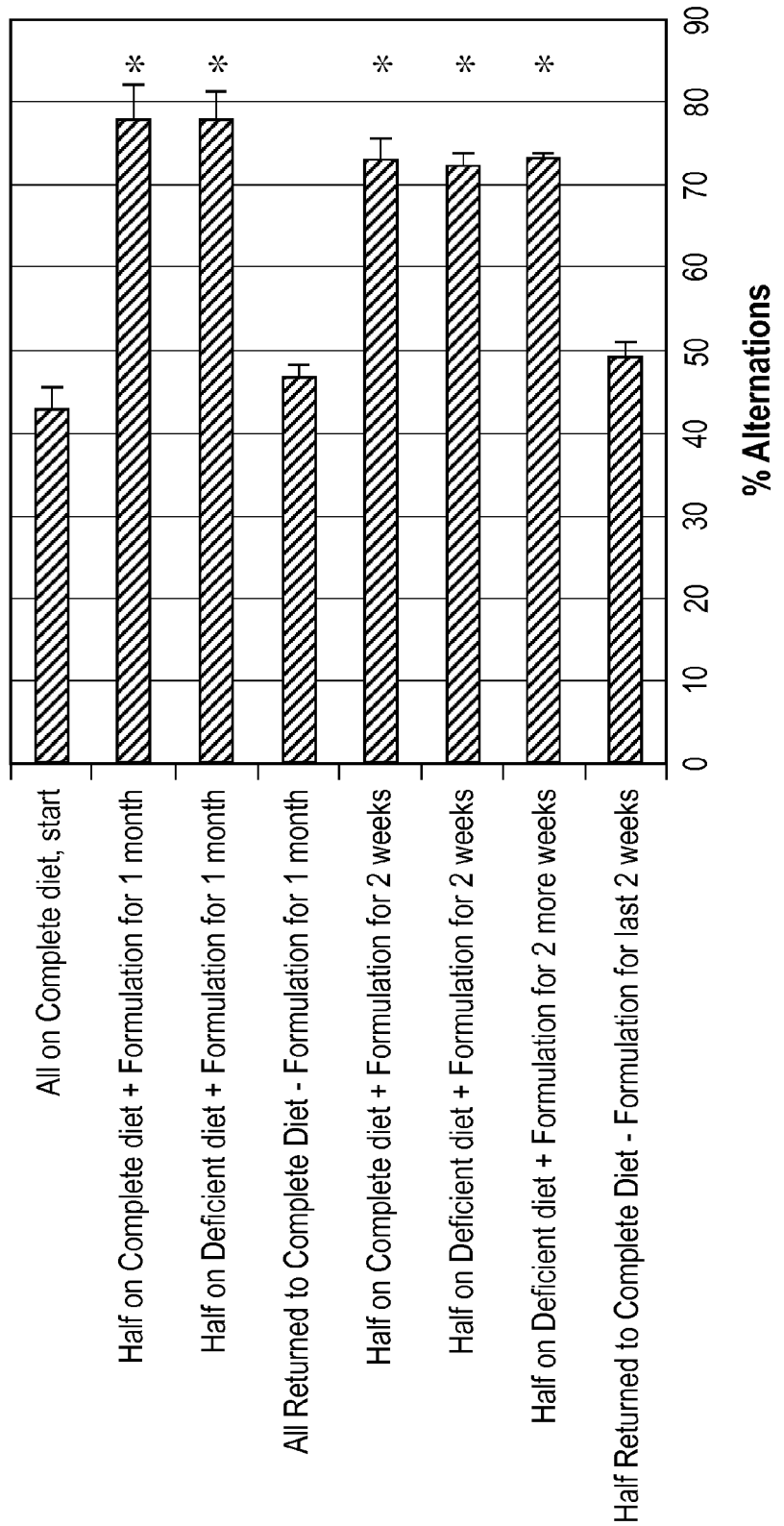
FIG. 1 graphically depicts improvement in cognitive performance in normal adult mice following supplementation with NAC, ALCAR and SAM. Normal mice (n=8 in 2 independent experiments) were maintained sequentially on the indicated diets, with or without supplementation with NAC, ALCAR and SAM ("formulation") for 1 month or 2 weeks as listed from the top to the bottom of the graph. Mice were subjected to Y maze analyses prior to the start of the experiment and at the end of each indicated interval, then were changed to the next diet. Values represent the mean±standard error of the mean in % alternations recorded for all mice in both experiments over a 5 min interval; values accompanied by an asterisk differed statistically from value obtained for mice on the complete diet ("start"). This data indicates a reversible improvement of about 70% in cognitive performance for mice receiving the formulation on either diet.

The present invention is based, at least in part, on the discovery of novel nutriceutical formulations which improve cognitive function in normal adults. The formulations of the invention have further been shown to improve cognition in adults diagnosed with neurodegenerative disease, e.g., early-stage and mid/late-stage Alzheimer's Disease. In patients diagnosed with neurodegenerative disease, the formulations of the invention have additionally been shown to improve mood and behavior, reduce depression, and decrease aggression. The formulations of the invention also have been found to improve cognitive function and reduce aggression in normal adult mice and mice expressing human ApoE4, a mouse model of Alzheimer's Disease.

Current treatments for Alzheimer's disease are pharmacological approaches, many of which impart significant side-effects and all of which provide only transient relief from cognitive decline. The development of non-prescription nutriceutical formulations is highly desirable as both a preventative measure, as well as to augment any pharmacological treatment approaches. Such nutriceutical formulations also are useful for normal subjects, e.g., normal adults seeking to improve cognitive function and mood and/or reduce aggression and depression.

A growing body of research indicates that nutritional deficiencies contribute to AD onset and progression. Key genetic and/or environmental factors may remain latent pending age-related decline in nutrition. This suggests the potential importance of early nutritional intervention, including preventative approaches prior to definitive diagnosis. Oxidative stress is a pivotal factor in AD, and is evident prior to cytopathological hallmarks of the disorder. Antioxidants therefore represent a potential preventative approach. Antioxidants such as vitamin E provide some, but not complete, neuroprotection in AD. Limitations of vitamin E are likely to be due at least in part to its lipohilic nature and resultant inability to quench cytosolic oxidative species, including those resulting from antecedent membrane oxidation. An additional approach may be to stimulate the production of endogenous antioxidants. The endogenous antioxidant glutathione (GSH), and activity of the associated enzyme glutathione S-transferase, are reduced in AD. Polymorphisms of this enzyme with diminished activity potentiate the impact of ApoE deficiency. Strategies to maintain appropriate GSH production may be useful as part of a therapeutic approach to delay the onset or progression of AD. GSH itself can not be taken up, but the GSH precursor N-acetyl cysteine (NAC) increases GSH production.

Folate deficiency contributes to many neurological and psychological disorders including AD. Folate- and B12-dependent reactions regenerate methionine from the neurotoxin homocysteine (which is related to the severity and progression of AD). The deleterious effects of folate deprivation are potentiated by deficiency in apolipoprotein E (ApoE), which itself increases oxidative stress and is associated with AD. Functional folate deficiency can also arise from polymorphisms in 5', 10' methylene tetrahydrofolate reductase (MTHFR, the enzyme that utilizes folate), which represent synergistic AD risk factors together with ApoE deficiency. Supplementation with folate and/or B12 in AD has generated conflicting results.

Folate deficiency decreases S-adenosylmethionine (SAM), the major methyl donor, which declines in normal aging and AD and may underlie the gradual hypomethylation of DNA that accompanies aging. ApoE deficiency also fosters a critical reduction in SAM and, since SAM is an essential cofactor for glutathione-S-transferase, restricts the ability of GSH to quench cytosolic oxidative species. Diminished SAM in AD may foster increased expression of presenilin (PS) leading to an increase in beta-amyloid (Abeta), the pathological hallmark of AD, and beta and gamma secretase activity, the enzymes responsible for the abnormal cleavage of the amyloid precursor protein. While SAM provided limited efficacy in clinical trials for depression, its effect in AD remains unknown.

Quenching of oxidative species, including those generated by Abeta and homocysteine, and increased DNA repair resulting from impaired DNA methylation (due to SAM depletion) can consume considerable energy and lead to ATP depletion, triggering neuronal apoptosis. Towards this end, acetyl-L-carnitine (ALCAR) (which prevents mitochondrial degeneration, increases ATP, and supports GSH production) was utilized in a clinical trial, but was ineffective against early-stage AD.

The novel nutriceutical formulations described herein contain components which synergistically provide neuroprotection against oxidative stress; decrease PS-1 expression, gamma-secretase activity, Abeta generation, and tau phosphorylation; increase glutathione, ATP, and acetylcholine; compensate for apolipoprotein E deficiency; prevent cognitive decline; and decrease aggression. Co-administration of the components of the nutriceutical formulations maintained and/or improved cognitive performance, behavioural symptoms and daily activities in early and mid/late stage Alzheimer's patients, indicating that they are useful in treating and/or reducing the symptoms associated with AD. The formulations of the invention have been further shown to improve cognitive performance in healthy adults, indicating that such formulations are also beneficial as a preventative measure in individuals seeking to prevent or delay the onset of AD, or who are seeking to improve cognitive performance and reduce aggression.

In certain aspects, the novel formulations of the invention include combinations of six vitamins, antioxidants and nutriceuticals that synergistically provide protection to brain cells. The fundamental components of the formulations of the invention are folic acid, vitamin B12, vitamin E, S-adenosyl methionine, N-acetyl cysteine, and acetyl-L-carnitine. The formulations of the invention can include some or all of these components. In preferred embodiments, the formulations include one or more components selected from folic acid, vitamin B12, and vitamin E, and one or more components selected from S-adenosyl methionine, N-acetyl cysteine, and acetyl-L-carnitine. In one embodiment, the formulation includes folic acid, vitamin B12, S-adenosyl methionine, and N-acetyl cysteine. In another embodiment, the formulation includes folic acid, vitamin B12, S-adenosyl methionine, and acetyl-L-carnitine. In another embodiment, the formulation includes folic acid, vitamin B12, N-acetyl cysteine, and acetyl-L-carnitine. In another embodiment, the formulation includes folic acid, vitamin E, S-adenosyl methionine, and N-acetyl cysteine. In another embodiment, the formulation includes folic acid, vitamin E, S-adenosyl methionine, and acetyl-L-carnitine. In another embodiment, the formulation includes folic acid, vitamin E, N-acetyl cysteine, and acetyl-L-carnitine. In another embodiment, the formulation includes vitamin B12, vitamin E, S-adenosyl methionine, and N-acetyl cysteine. In another embodiment, the formulation includes vitamin B12, vitamin E, S-adenosyl methionine, and acetyl-L-carnitine. In another embodiment, the formulation includes vitamin B12, vitamin E, N-acetyl cysteine, and acetyl-L-carnitine. An exemplary formulation of the invention includes folic acid, vitamin B12, vitamin E, S-adenosyl methionine, N-acetyl cysteine, and acetyl-L-carnitine. Another exemplary formulation includes folic acid, vitamin B12, S-adenosyl methionine, and N-acetyl cysteine. As described in further detail herein, folate and vitamin B12 raise levels of S-adenosyl methionine, and S-adenosylmethionine and N-acetyl cysteine together increase and form the antioxidant glutathione. Based on the observations set forth herein, these formulations are proposed to buffer neurons from oxidative attack or metabolic deficiencies, provide neurons with additional energy, aid neurons in utilization of antioxidants, and maintain neurotransmitter production. Accordingly, the formulations of the invention provide a novel pharmaceutical approach for improving cognition, mood and behavior, and for reducing depression and aggression, in normal adults and in adults diagnosed with neurodegenerative disease.

The formulations can be used or administered alone, or together in combination with other nutriceutical or pharmaceutical compositions. Nutriceutical or pharmaceutical compositions suitable for administration in combination with the formulations of the invention include nutriceutical or pharmaceutical compositions effective in improving cognition or reducing symptoms associated with a neurological disorder (e.g., Alzheimer's disease, Parkinson's disease, amyotrophic lateral sclerosis) or a mood disorder (e.g., depression, anxiety, aggression/agitation). Such compositions include, for example, haloperidol, risperidone, olanzapine, clozapine, ziprasidone, quetiapine, fluoxetine hydrochloride, paroxetine, citalopram, sertraline hydrochloride, nortriptyline, alprazolam, lorazepam, oxazepam, and buspirone. As the formulations of the invention increase production of acetylcholine, the formulations are proposed to act synergistically with pharmaceutical compounds or compositions that maximize acetylcholine availability by inhibiting its breakdown. Such cholinesterase inhibitors include, for example, donepezil, galantamine, and rivastigmine. Pharmaceutical compositions that have been shown to act synergistically in combination with agents that increase available acetylcholine are also proposed to act synergistically in combination with the formulations of the invention. Such compounds include, for example, those that target the glutamatergic system, e.g., memantine. As the formulations of the invention further support mitochondrial health, it is proposed that the formulations of the invention would augment treatment with pharmacological agents that regulate calcium influx into neurons, as critical increases in calcium can perturb mitochondrial function.

Based at least in part on the above observations, the invention features, in a first aspect, methods for improving cognitive performance in a subject, involving administering to the subject a formulation containing folate, vitamin E, vitamin B12, N-acetyl cysteine, acetyl-L-carnitine, and S-adenosyl methionine. In another aspect, the invention features methods for reducing aggression in a subject, involving administering to the subject a formulation containing folate, vitamin E, vitamin B12, N-acetyl cysteine, acetyl-L-carnitine, and S-adenosyl methionine. In yet another aspect, the invention features methods for improving mood and reducing depression in a subject, involving administering to the subject a formulation containing folate, vitamin E, vitamin B12, N-acetyl cysteine, acetyl-L-carnitine, and S-adenosyl methionine.

In one embodiment of these aspects, the subject is a mammal. In another embodiment, the subject is a mouse. In an exemplary embodiment, the subject is a human. In a related embodiment, the subject is a normal adult. In an alternative embodiment, the subject is an adult who suffers from or has been diagnosed with a neurodegenerative disorder. In one embodiment, the neurodegenerative disorder is Alzheimer's disease, Parkinson's disease, or amyotrophic lateral sclerosis (ALS). In a related embodiment, the neurodegenerative disorder is early stage or mid/late stage Alzheimer's disease. In another embodiment, the subject is at risk of developing a neurodegenerative disorder, such as Alzheimer's disease, Parkinson's disease, or amyotrophic lateral sclerosis (ALS). In a related embodiment, the neurodegenerative disorder is early stage or mid/late stage Alzheimer's disease.

In another embodiment of these aspects, the formulation is administered orally. In an alternative embodiment, the formulation is administered parenterally. In a further embodiment of these aspects, the formulation is administered as a unit dosage form. In an exemplary embodiment, the unit dosage form of the formulation comprises folate in a dose of about 2-10 µg/kg. In another embodiment, the unit dosage form of the formulation comprises vitamin E in a dose of about 0.2-0.7 IU/kg. In an exemplary embodiment, vitamin E is in the form of α-tocopherol. In another embodiment, the unit dosage form of the formulation comprises vitamin B12 in a dose of about 0.04-0.14 µg/kg. In another embodiment, the unit dosage form of the formulation comprises N-acetyl cysteine in a dose of about 4-14 mg/kg. In another embodiment, the unit dosage form of the formulation comprises acetyl-L-carnitine in a dose of about 3-12 mg/kg. In another embodiment, the unit dosage form of the formulation comprises S-adenosyl methionine in a dose of about 3-10 mg/kg. In another embodiment, the formulation additionally contains a pharmaceutically acceptable carrier. In an exemplary embodiment, the unit dosage form of the formulation contains 400 µg folate, 6 µg vitamin B12, 30 IU vitamin E, 400 mg S-adenosyl methionine, 600 mg N-acetyl cysteine, and 500 mg acetyl-L-carnitine.

In another aspect, the invention features compositions useful for practicing the methods of the invention. Such compositions contain folate, vitamin E, vitamin B12, N-acetyl cysteine, acetyl-L-carnitine, and S-adenosyl methionine. In one aspect, the compositions comprise folate, vitamin E, vitamin B12, N-acetyl cysteine, acetyl-L-carnitine, and S-adenosyl methionine. In another aspect, the compositions consist essentially of folate, vitamin E, vitamin B12, N-acetyl cysteine, acetyl-L-carnitine, and S-adenosyl methionine. In a further aspect, the compositions consist of folate, vitamin E, vitamin B12, N-acetyl cysteine, acetyl-L-carnitine, and S-adenosyl methionine.

In one embodiment of these aspects, the compositions contain folate in an amount equivalent to a dose of about 2-10 µg/kg when administered to a subject. In another embodiment of these aspects, the compositions contain vitamin E in an amount equivalent to a dose of about 0.2-0.7 IU/kg when administered to a subject. In an exemplary embodiment, vitamin E is in the form of α-tocopherol. In another embodiment of these aspects, the compositions contain vitamin B12 in an amount equivalent to a dose of about 0.04-0.16 µg/kg when administered to a subject. In another embodiment of these aspects, the compositions contain N-acetyl cysteine in an amount equivalent to a dose of about 4-16 mg/kg when administered to a subject. In another embodiment of these aspects, the compositions contain acetyl-L-carnitine in an amount equivalent to a dose of about 3-12 mg/kg when administered to a subject. In another embodiment of these aspects, the compositions contain S-adenosyl methionine in an amount equivalent to a dose of about 3-12 mg/kg when administered to a subject. In an exemplary embodiment, the invention features a composition containing about 400 µg folate, 6 µg vitamin B12, 30 IU vitamin E, 400 mg S-adenosyl methionine, 600 mg N-acetyl cysteine, and 500 mg acetyl-L-carnitine. In another embodiment of these aspects, the compositions of the invention are formulated for administration to a subject. In one embodiment, the composition is formulated as a dietary supplement. In another embodiment, the composition is formulated for use as a food additive. In related embodiments, the composition is formulated as either a solid, or as a liquid.

The invention also features kits containing the compositions of the invention. Accordingly, in one aspect, the invention features kits containing one or more compositions of the invention together with instructions for administration to a subject. In another aspect, the invention features kits containing one or more compositions of the invention together with one or more additional nutriceuticals and instructions for administration to a subject. In one embodiment of this aspect, the other nutriceuticals may include, for example, ginko biloba, fish oil, and apple juice. In yet another aspect, the invention features kits containing one or more compositions of the invention together with a set of cognitive exercises. These cognitive exercises may include, for example, crossword puzzles or sudoku puzzles.

The invention additionally features methods of treating a neurodegenerative disorder in a subject, involving administering a therapeutically effective amount of a composition of the invention to the subject, such that the disorder is treated. The invention further features methods of reducing symptoms associated with a neurodegenerative disorder in a subject, involving administering a therapeutically effective amount of a composition of the invention to the subject, such that the symptoms of the disorder are reduced. In one embodiment of these aspects, the neurodegenerative disorder may be Alzheimer's disease, Parkinson's disease, or amyotrophic lateral sclerosis (ALS). In a further embodiment, the neurodegenerative disorder may be early stage or mid/late stage Alzheimer's disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Various aspects of the invention are described in further detail in the following subsections.

I. Nutriceutical Formulations

A nutriceutical formulation of the invention includes combinations of the following six agents: folic acid, vitamin B12, vitamin E, S-adenosyl methionine, N-acetyl cysteine, and acetyl-L-carnitine. These components provide a number of benefits to neuronal cells, including minimizing the impact of oxidative stress and oxidative damage on neurons, which helps to ameliorate the effects of oxidative stress and oxidative damage during normal aging. These components also synergistically prevent several hallmarks of Alzheimer's Disease, and buffer the consequences of genetic and dietary AD risk factors. Components of the formulations of the invention have been shown to, for example, decrease production of Abeta, a protein which comprises the main constituent of amyloid plaques in the brains of Alzheimer's Disease patients (Chan A. and Shea T. B. (2007) J Neurochem: 102:753-760). In addition, components of the formulations of the invention decrease phosphorylation of the microtubule-associated protein tau, which aggregates into neurofibrillary tangles following abberant phosphorylation (Chan A. and Shea T. B. (2006) J Alz Dis: 9:399-405). Components of the formulations described herein are further involved in decreasing cellular levels of homocysteine, increasing production and efficacy of the antioxidant glutathione (Tchantchou F, Graves M, Ortiz D and Shea TB (2006) J Nutri Health Aging 10:541-544), and maintenance of production of the cognitive neurotransmitter acetylcholine, which declines in AD and is a major pharmacological target (Chan A, Tchantchou F, Graves V, Rozen R and Shea T B (2007) J Health Nutr Aging (in press)).

Importantly, the combination of components of the formulations has been discovered to be more effective than the individual components in the uses of the invention. This is, in part, because while the components can hypothetically act individually to ameliorate some potential biochemical factors contributing to cognitive decline, individual ingredients of the formulations have been used in prior preclinical and clinical studies with limited or no efficacy. As the results described herein indicate, the degree of efficacy of the particular formulations of the invention was completely unanticipated, indicating that these unique combinations synergistically provide neuroprotection.

The human brain consists of a multitude of different populations of neurons, each of which perform distinct functions in learning and memory. These neurons are not normally replaced, but rather must survive and function throughout our lifetime. As humans live for a longer period of time, most experience a decline in memory, reaction time, and cognitive ability with aging. At any given moment, the neurons of the brain can be divided into four distinct categories: those that are healthy, but are at risk for degeneration; those that have already undergone mild degeneration but can be rescued and returned to normal health and function by nutritional or pharmacological supplementation; those that have undergone extensive damage and, although still functional for a time are beyond repair, but can be prolonged by nutritional or pharmacological supplementation; and those that have degenerated. The formulations of the invention were rationally designed through extensive pre-clinical study to derive specific formulations that address the needs of an at-risk and/or damaged neuronal population, while also protecting healthy neurons in need of one or more components of the formulations and remaining benign to any neurons not requiring these components.

At any given moment, some of our neurons need buffering from de novo oxidative attack or metabolic deficiencies (i.e., neurons that are at risk or have undergone mild degeneration); this buffering is provided by vitamin E (for oxidative attack) or folate and B12 (for metabolic deficiencies). Others need buffering from more extensive, prior oxidative attack and metabolic deficiencies (i.e., neurons that have undergone extensive damage); this buffering is provided by N-acetyl cysteine (for prior oxidative attack; vitamin E cannot help prior attack) or folate and B12 (for metabolic deficiencies). Neurons in all stages may require extra bursts of energy at differing intervals (provided by acetyl-L-carnitine), and these neurons will, depending upon the severity of attack or deficiency, require varying amounts of S-adenosylmethionine (to keep their genetic expression in order, help utilization of their antioxidants, and maintain neurotransmitter production). With respect to neurons that have been extensively damaged, it is necessary to note that even when a given therapy is initiated, there may still be decline due to irreversible prior degeneration; this was evidenced in a prior test of the efficacy of vitamin E alone (Sano et al. (1997) N Eng J Med; 336: 1216), in which continued decline was observed among treated patients. Moreover, it is only when many neurons have fully degenerated that the effects of degeneration observed, as the cause of degeneration is antecedent by years or decades both in Alzheimer's and in normal aging. As the data presented herein indicate, the formulations of the invention maintain and actually improve cognition while reducing anxiety, aggression, irritability and depression. These latter conditions are critically important to the aging and Alzheimer's populations, as they are often the factors that predict collapse of family care-giver infrastructure and warrant nursing home care.

Nutriceutical formulations can be prepared using methods known in the art. The nutriceutical formulations of the invention contain four, five, or six of the following components: folic acid, vitamin B12, vitamin E, S-adenosyl methionine, N-acetyl cysteine, and acetyl-L-carnitine. These formulations contain ranges of amounts of the individual components. For example, the amount of folic acid to be administered with the other components for therapeutic use is between about 200 to 2400 µg folic acid per day. Specific therapeutic dosages within this range include 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, and 2400 µg/day. In an exemplary embodiment, the therapeutic dosage of folic acid is between about 400-800 µg/day. The therapeutic dosage of folic acid is equivalent to a dosage of between about 0.6 µg/kg per day to 55 µg/kg per day. Specific dosages within this range include dosages of about 0.1 µg/kg, 0.5 µg/kg, 1 µg/kg, 2.5 µg/kg, 5 µg/kg, 7 µg/kg, 10 µg/kg, 15 µg/kg, 20 µg/kg, 25 µg/kg, 30 µg/kg, 35 µg/kg, 40 µg/kg, 45 µg/kg, 50 µg/kg, and 55 µg/kg per day.

The amount of vitamin B12 to be administered with the other components for therapeutic use is between about 3 µg to 36 µg vitamin B12 per day. Specific therapeutic dosages within this range include 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 17, 18, 19, 20, 21, 22, 23, 24, 25, 26, 27, 28, 29, 30, 31, 32, 33, 34, 35, and 36 µg/day. In an exemplary embodiment, the therapeutic dosage of vitamin B12 is between about 6-12 µg/day. The therapeutic dosage of vitamin B12 is equivalent to a dosage of between about 0.02 µg/kg per day to 0.9 µg/kg per day. Specific dosages within this range include dosages of about 0.02 µg/kg, 0.03 µg/kg, 0.04 µg/kg, 0.05 µg/kg, 0.06 µg/kg, 0.07 µg/kg, 0.08 µg/kg, 0.09 µg/kg, 0.1 µg/kg, 0.2 µg/kg, 0.3 µg/kg, 0.4 µg/kg, 0.5 µg/kg, 0.6 µg/kg, 0.7 µg/kg, 0.8 µg/kg, and 0.9 µg/kg per day.

The amount of vitamin E to be administered with the other components for therapeutic use is between about 15 IU to 90 IU vitamin E per day. Specific therapeutic dosages within this range include 15, 20, 25, 27.5, 30, 35, 40, 45, 50, 55, 60, 65, 70, 75, 80, 85, and 90 IU/day. In an exemplary embodiment, the therapeutic dosage of vitamin E is between about 30-60 IU/day. The therapeutic dosage of vitamin E is equivalent to a dosage of between about 0.1 IU/kg per day to 2 IU/kg per day. Specific dosages within this range include dosages of about 0.1 IU/kg, 0.2 IU/kg, 0.3 IU/kg, 0.4 IU/kg, 0.5 IU/kg, 0.6 IU/kg, 0.7 IU/kg, 0.8 IU/kg, 0.9 IU/kg, 1 IU/kg, 1.2 IU/kg, 1.4 IU/kg, 1.6 IU/kg, 1.8 IU/kg, and 2 IU/kg per day. In an exemplary embodiment, vitamin E is α-tocopherol.

The amount of S-adenosyl methionine to be administered with the other components for therapeutic use is between about 200 mg to 2400 mg S-adenosyl methionine per day. Specific therapeutic dosages within this range include 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, 2000, 2100, 2200, 2300, and 2400 mg/day. In an exemplary embodiment, the therapeutic dosage of S-adenosyl methionine is between about 400-800 mg/day. The therapeutic dosage of S-adenosyl methionine is equivalent to a dosage of between about 1.4 mg/kg per day to 56 mg/kg per day. Specific dosages within this range include dosages of about 1.5 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 24 mg/kg, 28 mg/kg, 32 mg/kg, 36 mg/kg, 40 mg/kg, 45 mg/kg, and 55 mg/kg per day.

The amount of N-acetyl cysteine to be administered with the other components for therapeutic use is between about 300 mg to 3600 mg N-acetyl cysteine per day. Specific therapeutic dosages within this range include 300, 350, 400, 450, 500, 550, 600, 650, 700, 750, 800, 850, 900, 950, 1000, 1200, 1400, 1600, 1800, 2000, 2200, 2400, 2600, 2800, 3000, 3200, 3400, and 3600 mg/day. In an exemplary embodiment, the therapeutic dosage of N-acetyl cysteine is between about 600-1200 mg/day. The therapeutic dosage of N-acetyl cysteine is equivalent to a dosage of between about 2 mg/kg per day to 85 mg/kg per day. Specific dosages within this range include dosages of about 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, and 85 mg/kg per day.

The amount of acetyl-L-carnitine to be administered with the other components for therapeutic use is between about 250 mg to 3000 mg acetyl-L-carnitine per day. Specific therapeutic dosages within this range include 250, 300, 350, 400, 450, 500, 550, 600, 650, 700, 750, 800, 850, 900, 950, 1000, 1200, 1400, 1600, 1800, 2000, 2200, 2400, 2600, 2800, and 3000 mg/day. In an exemplary embodiment, the therapeutic dosage of acetyl-L-carnitine is between about 500-1000 mg/day. The therapeutic dosage of acetyl-L-carnitine is equivalent to a dosage of between about 1.5 mg/kg per day to 70 mg/kg per day. Specific dosages within this range include dosages of about 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 30 mg/kg, 35 mg/kg, 40 mg/kg, 45 mg/kg, 50 mg/kg, 55 mg/kg, 60 mg/kg, 65 mg/kg, and 70 mg/kg per day.

Also useful in the formulations of the invention are chemically similar compounds, for example, folate, natural or synthetic folate analogs (e.g., 4-amino folate, 2-deamino-2-hydroxyfolate, etc.), natural or synthetic vitamin B12 analogs, alternate bioactive forms of vitamin E (e.g., gamma-tocopherol, vitamin E esters including vitamin E succinate and vitamin E acetate, vitamin E salts including vitamin E phosphate, and other water soluble forms of vitamin E, including TROLOX®), and metabolic precursors or derivatives, or natural or synthetic analogs, of S-adenosyl methionine, N-acetyl cysteine, and acetyl-L-carnitine.

Although convenient for administration, it is not necessary for the agents or components of the nutriceutical formulations to be compounded together for administration to a subject. Instead, they can be administered concurrently, or in close enough succession so that the desired dosage level for all components is achieved in the bloodstream at the same time.

II. Methods of Testing Nutriceutical Formulation Efficacy (A) Use of Cell Culture Models for Testing Nutriceutical Formulation Efficacy In general, a nutriceutical formulation is formulated by combining appropriate concentrations of stock agent (e.g., in solution or solid) of the components in a medium. The components can be administered together, in rapid succession, or at intervals. A composition may be tested to determine whether it is an effective nutriceutical formulation in an in vitro cell culture system of primary, secondary, or immortalized neural cells, for example, cells that exhibit the molecular and biochemical characteristics of normal neural cells, or cells that exhibit at least some of the molecular and biochemical characteristics of a neurologic disorder. Examples of such cells and methods of evaluating the effects of the formulations are known in the art, and exemplary cells and methods are described below. Biochemical and physical criteria can be used to measure the ability of a nutriceutical formulation to ameliorate adverse events associated with aging and oxidative damage. Biochemical and physical criteria can additionally be used to measure the ability of a nutriceutical formulation to ameliorate adverse effects associated with a disorder in these cell culture systems. For example, a decrease in reactive oxygen species is indicative of effectiveness. In some cases, cells are treated with Abeta and the ability of a formulation to ameliorate at least one deleterious cellular response to Abeta is measured. Deleterious responses to Abeta include increased Reactive Oxygen Species (ROS), calcium influx, increased phosphorylation of tau, and apoptosis. A formulation that decreases ROS and/or a deleterious cellular response to Abeta is a candidate nutriceutical formulation or pharmaceutical formulation, because it has been demonstrated that quenching of ROS renders Abeta exposure benign (Ekinci et al., 1999, J. Biol. Chem., 274:30322-30327). Other methods can also be used to evaluate nutriceutical formulations. For example, methods useful for measuring expression of stress-induced genes are well-known in the art.

(B) Use of Animal Models for Testing Nutriceutical Formulation Efficacy

Animal models are likewise useful for evaluating the efficacy of a nutriceutical formulation. Nutriceutical formulations can be evaluated in vivo using an animal model, for example, an animal model of normal aging or an animal model of a specific neurologic disorder. Examples of animal models of aging include, for example, mice having a genomic mutation in the exonuclease domain II (ExoII) of a mitochondrial DNA polymerase gamma (PolG) gene and mice deficient in expression of WRN and telomerase (a mouse model of Werner's Syndrome), in addition to other models known in the art. Examples of animal models of neurologic disorders include a mouse model of familial ALS wherein mice express a mutant form of the superoxide dismutase gene, and a rat model of ALS in which axotomy of facial axons in neonatal rats causes retrograde cell degeneration (Cleveland et al., Neurology, 47 (Suppl 2): S54-61, 1996; Dal Canto, Clin. Neurosci., 2:332-337, 1996; and Price et al., Ciba Found. Symp., 196:3-13, 1996).

Examples of animal models for AD are the PDAPP (V717F) transgenic mouse (Johnson-Wood et al., Proc. Natl. Acad. Sci. USA, 94:1550-1555, 1997), mice expressing the human E4 allele of ApoE, mice expressing the human form of the protein Tau, and other transgenic mouse lines in which expression of the amyloid precursor protein (APP) gene is affected (Reaume et al., J. Biol. Chem., 271:23380-23388, 1996; Hsiao et al., Science, 276:99-102, 1996; and Games et al., Nature, 373:523-527, 1995). In addition, animal models of Parkinson's disease are known in the art and can be generated, for example, by treating young animals with 1-methyl-4-phenyl-1,2,3,6-tetrahydropyridine (MPTP; e.g., Tatton, Mov. Disord., 8 Suppl 1, S20-30, 1993; and Przedborski et al., Proc. Nat. Acad. Sci., USA, 93:4565-4571). Animal models are also used for studying the ability of nutriceutical formulations to affect spinal cord transplants. Such models are known in the art (e.g., Tessler et al., Adv. Neurol., 72:291-303, 1997).

As an example of how an animal model can be used to evaluate nutriceutical formulations of the invention, a transgenic mouse that expresses a neurofilament-beta galactosidase fusion protein (Eyer and Peterson, 1994, Neuron 12:389-405) can be used to evaluate the effects of a formulation on neurofilament phosphorylation and localization. Such mice do not carry out complete axonal transport of neurofilaments, but instead accumulate neurofilaments within neuronal perikarya. A nutriceutical formulation or pharmaceutical formulation is administered to such a mouse and the gross motor function and cellular morphology, especially the distribution of neurofilaments within cells, is evaluated over time in treated and untreated mice. Decreased accumulation of neurofilaments within the perikarya of neurons indicates that the nutriceutical formulation or pharmaceutical formulation is useful for correcting this defect. Additional biochemical indications can also be examined to determine the efficacy of nutriceutical formulations, for example by examining the change in markers characteristic of aging and/or neurological disorders in a population of test animals administered the formulations, compared with test animals administered placebo. Such biochemical indications include expression of presenilin-1 and Abeta, and expression or activity of gamma-secretase. Behavioral indications may also be used to evaluate the efficacy of nutriceutical formulations. Such behavioral indications include, for example, maze tests and tests measuring aggression. These tests are known in the art, and are also described in further detail in the examples provided herein.

Nutriceutical formulations can also be evaluated for their efficacy in preventing or ameliorating the effects of Alzheimer disease using an animal model, examples of which are provided herein. In one example, a transgenic mouse that overexpresses the 695-amino acid form of human Abeta appears to have normal learning and memory at 3 months of age (Hsiao et al., Science, 274:99-102, 1996). However, by 9 to 10 months, these animals are impaired. This pattern mimics the symptoms of Alzheimer disease in humans. The effects of a nutriceutical formulation on ameliorating behavioral and biochemical symptoms in these mice are evaluated after administering a nutriceutical formulation to these mice both early in life and after symptoms begin to develop. Mice are evaluated for the development or progression of learning and memory disorders as well as for pathophysiologic and biochemical abnormalities such as the presence of plaques in cortical and limbic structures of the brain. Prevention of the onset or progression of symptoms, or the amelioration of existing symptoms, indicates that the nutriceutical formulation is effective for treating Alzheimer disease or Parkinson's disease in humans.

Other animal models in which the animal carries one or more mutations associated with a neurologic disorder, such as mice that express the human E4 allele of the ApoE gene, or mice that are ApoE−/−, a genotype associated with Alzheimer's disease, are likewise useful in testing nutriceutical formulations. Animals with or without such mutations that have or have not been administered such nutriceutical formulations can be subjected to dietary/environmental distress such as folate deprivation or inclusion of dietary iron to induce biochemical and/or cognitive symptoms that can be measured in assays used to determine the efficacy of the nutriceutical formulations.

Other parameters of neuronal stress that are known in the art, examples of which are described herein, can be studied using tests known in the art, as well as those described herein, to evaluate the ability of a nutriceutical formulation to ameliorate symptoms associated with normal aging, oxidative stress, or neurodegenerative disorders. Such tests include measuring the presence of reactive oxygen species (ROS), or thiobarbituric acid-reactive substances (TBARs) resulting from same, in neuronal tissue in various transgenic mice models of Alzheimer's disease or Parkinson's disease, as well as comparisons of younger and aged normal mice.

In general, to evaluate whether a nutriceutical formulation or pharmaceutical formulation is useful for treating a neurologic disorder, an animal or human with symptoms or predisposition to a neurological disorder is treated with the formulation. After an appropriate treatment regime, the animal or human is examined for improvement or arrest of symptoms of the disorder. In the case of ALS, this can be stopping or slowing motor neuron degeneration. In Alzheimer disease, positive effects of a formulation can include improvement in memory, inhibition or arrest of progressive memory loss, decrease in anxiety or aggression, improvement in mood, decrease in the concentration of Abeta in spinal fluid, reduction in the rate of accumulation of amyloid plaques and/or neurofibrillary tangles, and reduction of ROS. Improvements detected in Parkinsonian conditions can be slowing or stopping degradation of motor function, particularly improvement of bradykinesia and akinesia, and decreased loss of cells in the substantia nigra. In all cases, animal models and cell culture systems are also useful for evaluating possible deleterious effects of a formulation.

The effects of a nutriceutical formulation or pharmaceutical formulation on neural cells, neurons, higher function, and behavior can also be evaluated in a human. In general this occurs after testing in an animal model. In such tests, for example, administration of an effective amount of a formulation to a healthy adult will result in an improvement in cognitive function, indicated by improvement on cognitive tests, including those known in the art and those described herein (e.g., Trail Making Tests A and B). Administration of an effective amount of a formulation to a healthy adult will additionally or alternatively result in an improvement in mood and/or a reduction in aggression, indicated by psychological evaluation or observations made by the subject and/or the family members of the subject. Administration of an effective amount of a formulation to a human subject diagnosed with Alzheimer's disease will result in slowing or stopping the progression of symptoms such as memory loss and poor or decreased judgment, and additionally or alternatively will positively impact personality, mood, aggression, and other behaviors, a change in which is associated with AD. The levels of ROS in the blood or cerebral-spinal fluid (CSF) can also be measured, and an effective formulation is one which results in a decrease ROS. In patients with ALS, the progression of symptoms such as muscular weakness and atrophy are slowed or halted by an effective formulation. Successful treatment of patients with Parkinson's disease is indicated by the slowing or stopping of the progression of symptoms such as muscular rigidity, resting tremor, or postural instability. In all disorders, physical, behavioral, and biochemical evaluation is performed using methods known in the art (e.g. *The Merck Manual, Sixteenth Edition*, 1992, R. Berkow, ed., Merck Research Laboratories, Rahway, N.J.).

III. Administration of Nutriceutical Formulations

One potential obstacle to administration of formulations targeting neuronal cells is that compounds may not effectively cross the blood-brain barrier, or may do so only in the presence of additional agents. The agents used in the nutriceutical formulations of the invention have been shown (directly or indirectly) to cross, or are predicted to cross, the blood-brain barrier (BBB). Moreover, the BBB becomes compromised and more permeable during oxidative stress (Argawal and Shulka, 1999, Neurochem. Res., 24:1507-1514); thus the agents used in nutriceutical and pharmaceutical formulations are likely to cross the blood-brain barrier in affected individuals. Furthermore, nutriceutical formulations of the invention cause a reduction in the total body burden of reactive oxygen species, thus reducing the level of reactive oxygen species in the brain.

The nutriceutical formulations for use in accordance with the present invention can be formulated in a conventional manner using one or more physiologically acceptable carriers or excipients. Agents used in the formulations and their physiologically acceptable salts and solvates can be prepared for administration by various methods. In an exemplary embodiment, administration of the formulations is oral. In an alternative embodiment, administration is parenteral, e.g., intravenous, subcutaneous, intramuscular, intracranial, intraorbital, ophthalmic, intraventricular, intracapsular, intraspinal, intracisternal, intraperitoneal, or transmucosal. The compounds can be formulated in various ways, according to the route of administration.

For oral administration, the formulations can take the form of, for example, tablets or capsules, prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice, e.g., apple juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). Other suitable non-aqueous vehicles may include neuroprotective foods, e.g., fish oil, flax seed oil, etc. The preparations can also contain buffer salts, flavoring, coloring and sweetening agents as appropriate.

Preparations for oral administration may be provided as a unit dosage form, for example, as tablets, capsules, etc. These can be presented in blister packs or in multi-dose containers. Preparations for oral administration can also be suitably formulated to give controlled release of the active compound.

For buccal or sublingual administration the formulations can take the form of tablets or lozenges formulated in conventional manner. The formulations can be prepared for parenteral administration by injection, for example, by bolus injection or continuous infusion. Formulations for injection can be presented in unit dosage form, for example, in ampoules or in multi-dose containers, with an added preservative. The formulations can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use.

The formulations can also be prepared in rectal compositions such as suppositories or retention enemas, for example, containing conventional suppository bases such as cocoa butter or other glycerides.

The formulations can also be provided as a depot preparation. Such long acting formulations may be administered by implantation (for example subcutaneously or intramuscularly) or by intramuscular injection. Thus, for example, the formulations can be prepared with suitable polymeric or hydrophobic materials (for example as an emulsion in an acceptable oil) or ion exchange resins, or as sparingly soluble derivatives, for example, as a sparingly soluble salt.

Because the action of a nutriceutical formulation or a pharmaceutical formulation can be in the central nervous system, delivery techniques can be designed to permit the formulation to cross the blood-brain barrier or to enhance the ability of the formulation to cross the blood-brain barrier. Such techniques are known in the art (for example, see PCT WO 89/10134, Cloughesy and Black, J. Neurooncol., 26:125-132, 1995; and Begley, J. Pharm. Pharmacol., 48:136-146, 1996, all of which are incorporated herein in their entirety). Components of a formulation can also be modified (e.g., chemically) using methods known in the art to facilitate their entry into the CNS.

In some cases, it may be desirable to deliver a nutriceutical formulation directly to the nervous system, especially when one or more components of a formulation do not cross the blood-brain barrier. Examples of such methods are intraventricular injection (Kordower et al., Exp. Neurol., 124:21-30, 1993) or installation of an osmotic pump (e.g., an Alzet® pump). Another example of such a method is to surgically place an Omaya reservoir-shunt with in-line filter into the cisternal space. A nutriceutical formulation or a pharmaceutical formulation in an appropriate excipient (e.g., phosphate-buffered saline) is instilled into the shunt by injection on a prescribed basis. In all cases, consideration is given to the appropriate formulation used for specific forms of delivery.

For administration by inhalation, a nutriceutical formulation is delivered, for example, as an aerosol spray with the use of a suitable propellant, for example, dichlorodifluoromethane, trichlorofluoromethane, dichlorotetrafluoroethane, carbon dioxide, or other suitable gas. Other suitable methods of nasal delivery known in the art can be used, including those that facilitate delivery of a predetermined dosage.

The formulations can be presented in a pack or dispenser device, which may contain one or more unit dosage forms containing the active ingredient. The pack may, for example, comprise metal or plastic foil, such as a blister pack. The pack or dispenser device can be accompanied by instructions for administration.

The therapeutic formulations of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol.

Methods useful for making formulations are known in the art and can be found in, for example, *Remington's Pharmaceutical Sciences* (Gennaro, ed., Williams & Wilkins, Baltimore, Md.).

It is not necessary for all of the components of a nutriceutical formulation to be administered in the same excipient, in the same form, or delivered at precisely the same time during a day. However, the components should be administered so they are present in the treated subject at the same time (e.g., present in a cell that is the target of treatment), and thus, one formulation, including all components, is generally provided in a convenient dosage form. This condition of treatment can be ascertained by assaying the appropriate body fluid (e.g., blood, plasma, serum, or cerebrospinal fluid) for the presence of components of a formulation or their metabolites. When monitoring the concentrations of agents, attention must be paid to differential accumulation of agents and/or their metabolites in the particular body fluid being tested. For example, folate has been reported to be concentrated four-fold within spinal fluid over that observed within plasma; moreover, the ability to concentrate folate within central nervous tissue declines in Alzheimer's disease (Snowdon et al., 2000, Am. J. Clin. Nutr., 71:993-998).

IV. Other Uses

A nutriceutical formulation can also be used to promote neuronal survival, and minimize secondary degeneration of endogenous neurons that is due to trauma.

The nutriceutical formulations can also be used to prevent or treat ischemia. For example, they can be administered as described herein in conjunction with procedures and devices such as transplantation (e.g., of neural tissue), implantation, and prosthetics. Administration can be systemic or directly to the site susceptible to ischemia such as by a shunt to a surgical site. Appropriate concentrations of the components of a nutriceutical formulation or a pharmaceutical formulation to be used for this purpose can be determined, for example, using methods described herein in model systems known in the art and in animal and human patients.

The nutriceutical formulations of the invention may be components in kits. These kits can also include instructions for administration of the formulations to a subject, and optionally may include one or more other nutriceuticals, e.g., ginko biloba, fish oil, apple juice, flax seed oil, and other nutriceutical foods or formulations known in the art. The nutriceutical formulations may also be provided in kits which additionally include puzzles or cognitive exercises, e.g., crossword puzzles, sudoku puzzles, and other cognitive games or exercises known in the art. These kits may additionally include instructions for administration, and/or other nutriceutical foods or formulations.

This invention is further illustrated by the following examples, which should not be construed as limiting. The contents of all references, patents and published patent applications cited throughout this application are incorporated herein by reference.

EXAMPLES

Example 1

Improvement in Cognitive Performance in a Pre-Clinical Study using Normal Adult Mice The objective of the study described herein was to examine the efficacy of a nutriceutical formulation on cognitive performance in normal adult mice. Groups of normal C57B/6 mice, and mice of the same genetic background but expressing human ApoE4 (n=8 in 2 independent experiments, 9-12 months of age) received a standard AIN-76 diet (Purina/Mother Hubbard, Inc.), or the same diet but lacking folate and vitamin E, and supplemented with iron (50 g/500 g total diet) as a pro-oxidant (defined as the "deficient diet") for 2 weeks to 1 month. Additional groups received these diets supplemented with a combination of N-acetyl cysteine (NAC, 5 g/kg total wet weight of diet); acetyl-L-carnitine (ALCAR, 1 g/kg diet); and S-adenosylmethionine (SAM, 100 mg/kg). These dietary supplements are proposed to act in multiple biological pathways. For example, NAC is an antioxidant and glutathione precursor that buffers Abeta neurotoxicity and prevents cognitive decline, ALCAR raises ATP levels, protects neuronal mitochondria, buffers Abeta neurotoxicity and supports cognitive performance, and SAM facilitates glutathione usage, reduces oxidative damage to brain tissue, prevents cognitive decline and maintains acetylcholine levels.

Cognitive impairment was monitored using a standard Y maze test as described (Chan et al., 2006; Mihalik et al., 2003). The pattern of exploration of the Y maze was recorded over 5 min intervals for each mouse. The frequency in which mice visited each of the 3 arms in succession during any 3-arm visitation sequence versus the total visitations defines the "% alternation." The same mice were sequentially maintained on complete or deficient diets, with and without supplementation with NAC, ALCAR and SAM, and subjected to Y maze tests at the end of each interval. Performance in the Y maze tests for various diets were statistically compared to "starting" values obtained for the respective mice (i.e., maintained on the complete diet) via Student's t test.

Supplementation of the complete diet with NAC, ALCAR and SAM increased the cognitive performance of normal mice as ascertained by the Y maze by approximately 70% within 1 month, as shown in FIG. 1. A similar increase was observed following supplementation with these agents even when mice were maintained on the deficient diet (see FIG. 1). This increase in cognitive performance was reversible; values returned to those observed prior to the start of the experiment within 2 weeks of withdrawal of supplementation. A second round of supplementation with NAC, ALCAR and SAM again similarly increased cognitive performance, while its withdrawal once again restored performance to baseline levels (see FIG. 1).

These findings demonstrate that combined treatment with NAC, ALCR, and SAM improves cognitive performance in normal mice. Prior studies demonstrated that SAM administered in isolation did not improve the performance of normal mice (Chan et. al. 2007), indicating that SAM, NAC, and ALCAR may function synergistically to promote cognition.

Example 2

Improvement in Cognitive Performance in Normal Adult Volunteers

Figure 2:
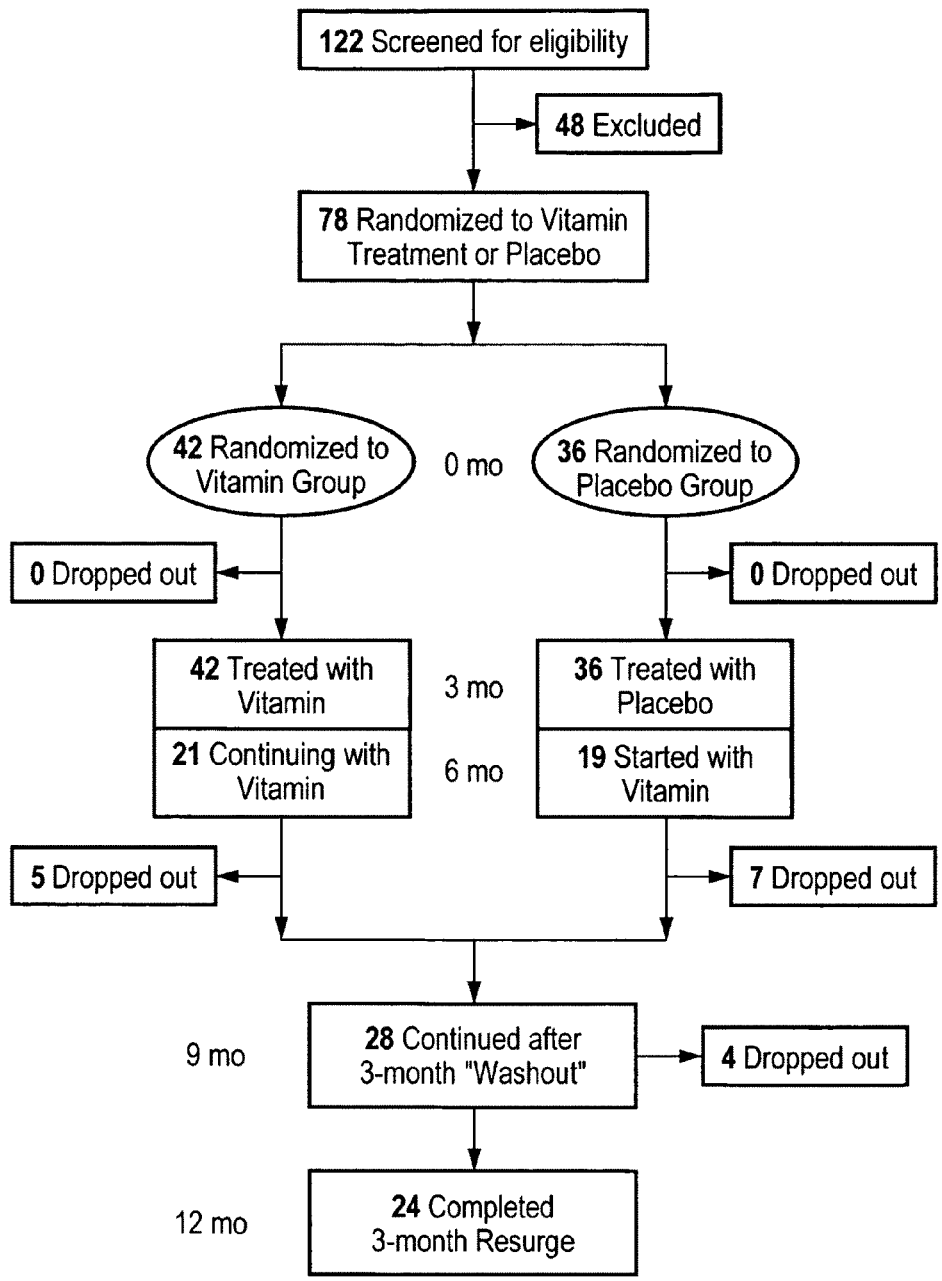
FIG. 2 depicts the study design and clinical trial profile of a one-year study designed to evaluate the efficacy of a nutriceutical formulation for improving cognitive performance in nondemented adults.

The objective of the study described herein was to examine the efficacy of a nutriceutical formulation on cognitive performance in cognitively normal seniors. More than ninety normal adults aged 40-73 without dementia participated in a 3-month double-blind, placebo-controlled study of Formulation A, containing folate at a dosage of about 2-20 µg/kg, vitamin E at a dosage of about 0.2-1.4 IU/kg, vitamin B12 at a dosage of about 0.04-0.28 µg/kg, N-acetyl cysteine at a dosage of about 4-28 mg/kg, acetyl-L-carnitine at a dosage of about 3-24 mg/kg, and S-adenosyl methionine at a dosage of about 3-20 mg/kg. Participants were asked to maintain their normal dietary regimen and vitamin intake throughout the course of the study. During the randomized, double-blind, placebo-controlled study, patients were randomized to receive 2 capsules daily, each containing either a combination of 400 ug of folic acid, 6 ug of Vitamin B12, 30 IU Vitamin E (as alpha-tocopherol), 400 mg of S-adenosylmethionine, 600 mg of N-acetyl cysteine, and 500 mg of Acetyl-L-carnitine, or a placebo. 42 individuals received Formulation A and 38 received placebo. The study design is outlined in FIG. 2. 7-day dietary records were obtained to determine daily caloric and vitamin intake.

Prior to and after 3 months the participants completed cognitive evaluations, including Trail-making Tests A and B (TMT). Trail-making test A is a timed test which asks participants to connect a series of dots numbered consecutively, and quantifies psychomotor performance. Trail-making test B asks participants to connect dots alternating in increasing number and letter (1, A, 2, B, 3, C, etc.), which quantifies both psychomotor performance and executive function. The score for A was subtracted from B to isolate executive function. Scores were normalized by standard methods according to age and education level. Patients who continued in the open-label extension were tested at each additional 3-month period. All baseline data for participants was initially pooled to obtain an overall average performance, and then parsed out at 3, 6, 9 and 12 months (continued open-label versus delayed start participants). Statistical analysis was performed for outcome measures using the Student's t test. The mean rates of change during the double-blind period (weeks 0-12) were compared with the mean rates of change in the open label, washout, and resurge periods for the TMT.

Figure 3:
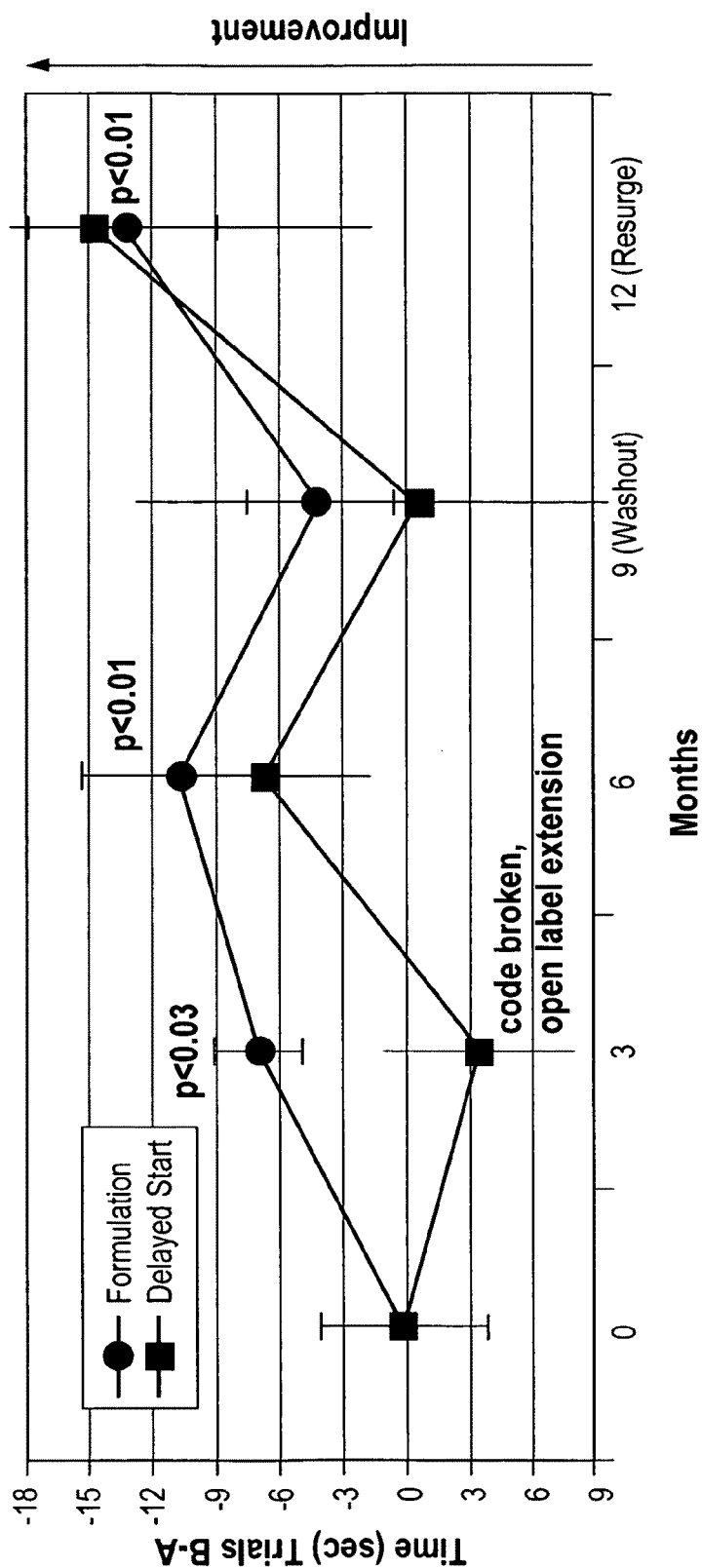
FIG. 3 graphically depicts improvement in cognitive performance, determined by the mean change from baseline in the Trail Making Test, in a double-blind, placebo-controlled study of Formulation A. A decrease in the number of seconds taken to complete the Trail Making Test is indicative of improvement. Participants receiving Formulation A show a steady increase in performance. The delayed start group attained the same level of improvement after 3 months receiving Formulation A as was achieved by the Formulation group after their first three months. Participants returned to baseline performance following a three-month reprieve from Formulation A (washout phase). Participants again demonstrated improvement following resumption of Formulation A (re-surge phase).

As indicated in FIG. 3, individuals receiving Formulation A improved versus baseline within 3 months (p<0.03). Individuals receiving Formulation A also differed from those receiving placebo. Individuals receiving placebo did not differ from baseline at 3 months, as is further shown in FIG. 3. Fifty-four of these individuals continued in our open-label extension (22 of whom originally received Formulation A, and 21 of whom originally received placebo). By 6 months, individuals continually receiving Formulation A improved versus baseline (p<0.01). Individuals originally receiving placebo improved following the 3 month Formulation A extension to the level statistically identical to that achieved by those originally receiving Formulation A at 3 months.

At the 6-month time point, all individuals enrolled in the study stopped taking Formulation A. After 3 months without Formulation A (9-month time point), cognitive performance was measured using Trail-making Tests A and B. As indicated in FIG. 3, the performance of individuals following this 3 month "wash" period returned to baseline. Formulation A was then administered to 20 of these individuals in a second open-label test for an additional 3 months, after which time these individuals again demonstrated a statistically-significant (p<0.01) increase in performance (see FIG. 3, 12-month time point). Individuals who had originally taken the formulation improved by an average of 13.3±4.4 seconds, while those who had originally taken placebo improved by an average of 14.5±12.8 seconds. The combined values for these two groups in this second open-label round differed significantly (p<0.03) from baseline. Loss of this improved performance following withdrawal of Formulation A, and restoration of improved performance following resumption of Formulation A both argue against any potential contribution of a "learning effect" to performance, and further are consistent with the need to maintain consumption of vitamins or nutriceuticals in order to sustain their effect. A single adverse event was reported in this trial (skin rash from a self-reported hyperallergenic participant), which resolved within 48 hours after discontinuation of treatment.

Figure 4:
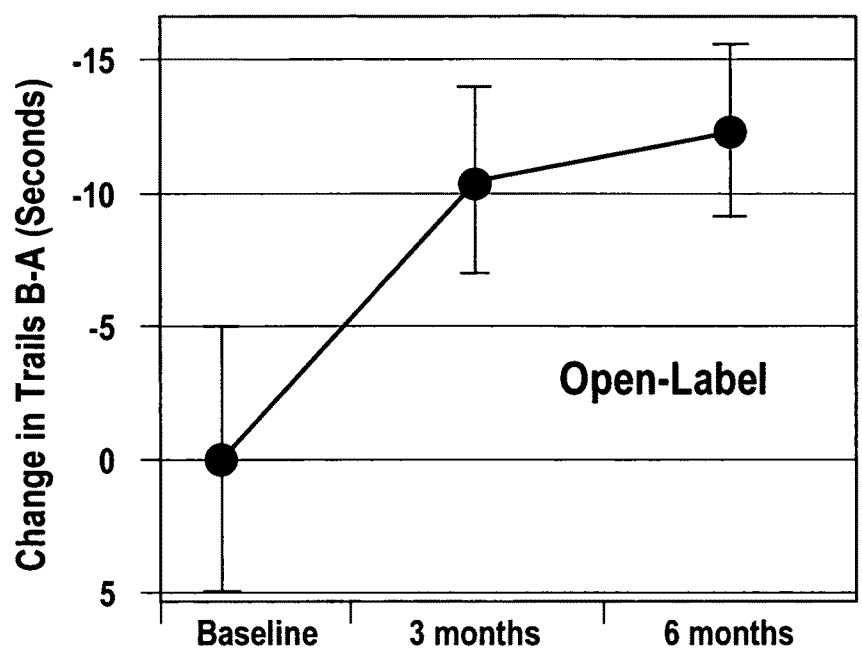
FIG. 4 graphically depicts improvement in cognitive performance in an open-label trial in which 35 healthy individuals received Formulation A over 6 months.

A second, multi-site open-label trial was conducted in which 35 healthy individuals received Formulation A over six months. These individuals completed the same Trail-making tests described above, and demonstrated similar levels of improvement compared with individuals enrolled in the double-blind, placebo-controlled study described herein (see FIG. 4). Statistical significance was observed at 6 months (p<0.03).

These findings indicate that Formulation A improves cognitive function in normal adults. In addition, Formulation A was shown to be safe and well-tolerated throughout the 12-month study period. In conclusion, the data presented herein demonstrate a role for Formulation A as a low-cost, over-the-counter neuroprotectant that may maintain neuronal health prior to dementia, and delay the decline associated with Alzheimer's disease.

Example 3

Figure 5:
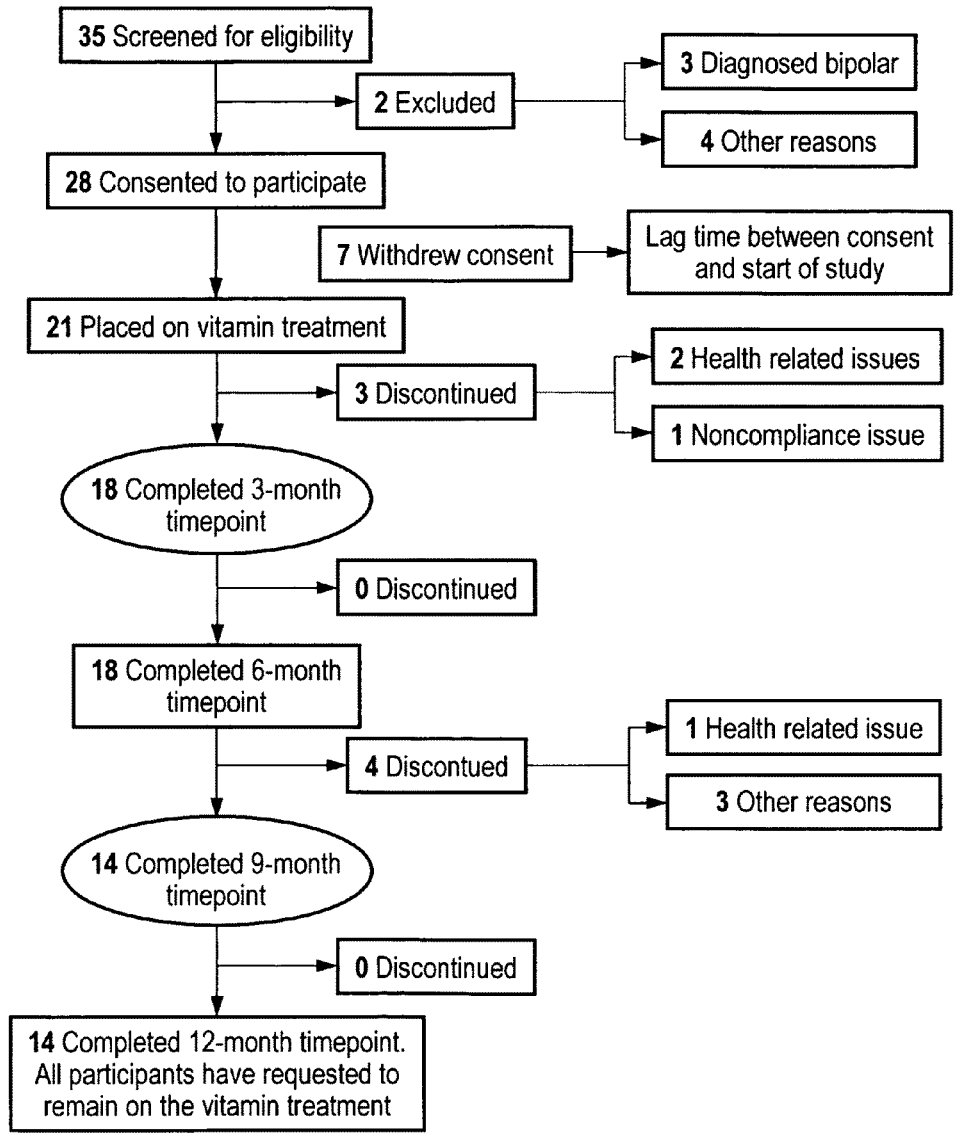
FIG. 5 depicts the study design and clinical trial profile of a one-year study designed to evaluate the efficacy of a nutriceutical formulation in individuals having early-stage Alzheimer's Disease.

Improvement in Cognitive Performance in Adults Diagnosed with Early Stage Alzheimer's Disease The objective of the study described herein was to examine the efficacy of a nutriceutical formulation on memory and cognitive performance in patients with early-stage Alzheimer's Disease. An open-label trial was conducted in which eighteen early-stage free-living Alzheimer patients received Formulation A, containing folate at a dosage of about 2-10 µg/kg, vitamin E at a dosage of about 0.2-0.7 IU/kg, vitamin B12 at a dosage of about 0.04-0.14 µg/kg, N-acetyl cysteine at a dosage of about 4-14 mg/kg, acetyl-L-carnitine at a dosage of about 3-12 mg/kg, and S-adenosyl methionine at a dosage of about 3-10 mg/kg. Patients received 2 capsules daily, each containing a combination of 400 ug of folic acid, 6 ug of Vitamin B12, 30 IU Vitamin E (as alpha-tocopherol), 400 mg of S-adenosylmethionine, 600 mg of N-acetyl cysteine, and 500 mg of Acetyl-L-carnitine. The study design is outlined in FIG. 5. Inclusion criteria were as follows: (1) clinical diagnosis of early-stage AD (according to the NINCDS criteria for probable AD; 61), (2)≥50 years of age, (3) no history or diagnosis of Bipolar Disorder (since SAM is contraindicated for bipolar disorder; 42), and (4) ineffectiveness of and/or adverse events with certain prescribed AD pharmaceuticals. DRS-II scores normalized for age and education level characterized participants as having mild to moderate AD (Mattis Dementia Rating Scale; 62). Participants were asked to maintain their normal dietary regimen and vitamin/medication intake throughout the course of this study. Although not a specified inclusion criterion, all participants had at least one family member caregiver who provided evaluations. Participants and caregivers were informed that they would receive NF for 12 months, and could elect for continued participation beyond 12 months, and that only serious adverse events, rather than lack of efficacy, could prompt exclusion from the study.

At baseline and at 3 month intervals for a total of 12 months, participants completed the Dementia Rating Scale 2 (DRS-2) and the Clox Drawing Test, each of which assess neuropsychological performance. Caregivers completed the Alzheimer's Disease Cooperative Study-Activities of Daily Living (ADCS-ADL), which assesses ability to engage in day-to-day activities, and the 12-Item Neuropsychiatric Inventory (NPI), which determines the degree to which abnormal behavior affects the patient's well-being, respectively. Participants were offered the opportunity to continue receiving Formulation A beyond the 12-month trial with a requirement for caregiver reports only. A subset (7) of these caregivers supplied ADCS-ADL and NPI information for their family members at 18 months. For statistical analyses, each participant's baseline score was subtracted from scores at subsequent intervals. Resultant paired differences were averaged and a 2-tailed t distribution was calculated for each interval vs. baseline with 13 degrees of freedom (i.e., n−1); values were considered statistically significant if p<0.05. The effect size was as calculated using raw scores at each time interval according to the formula: (mean at treatment time)− (mean at baseline)/standard deviation of baseline. Values>0.2 were considered clinically-significant; values>0.8 were considered to have large clinical significance (Cohen, J. *Statistical power analysis for the behavioral sciences (2$^{nd}$ edition)*. Hillsdale, N.J.: 1988; Lawrence Erlbaum).

Figure 6:
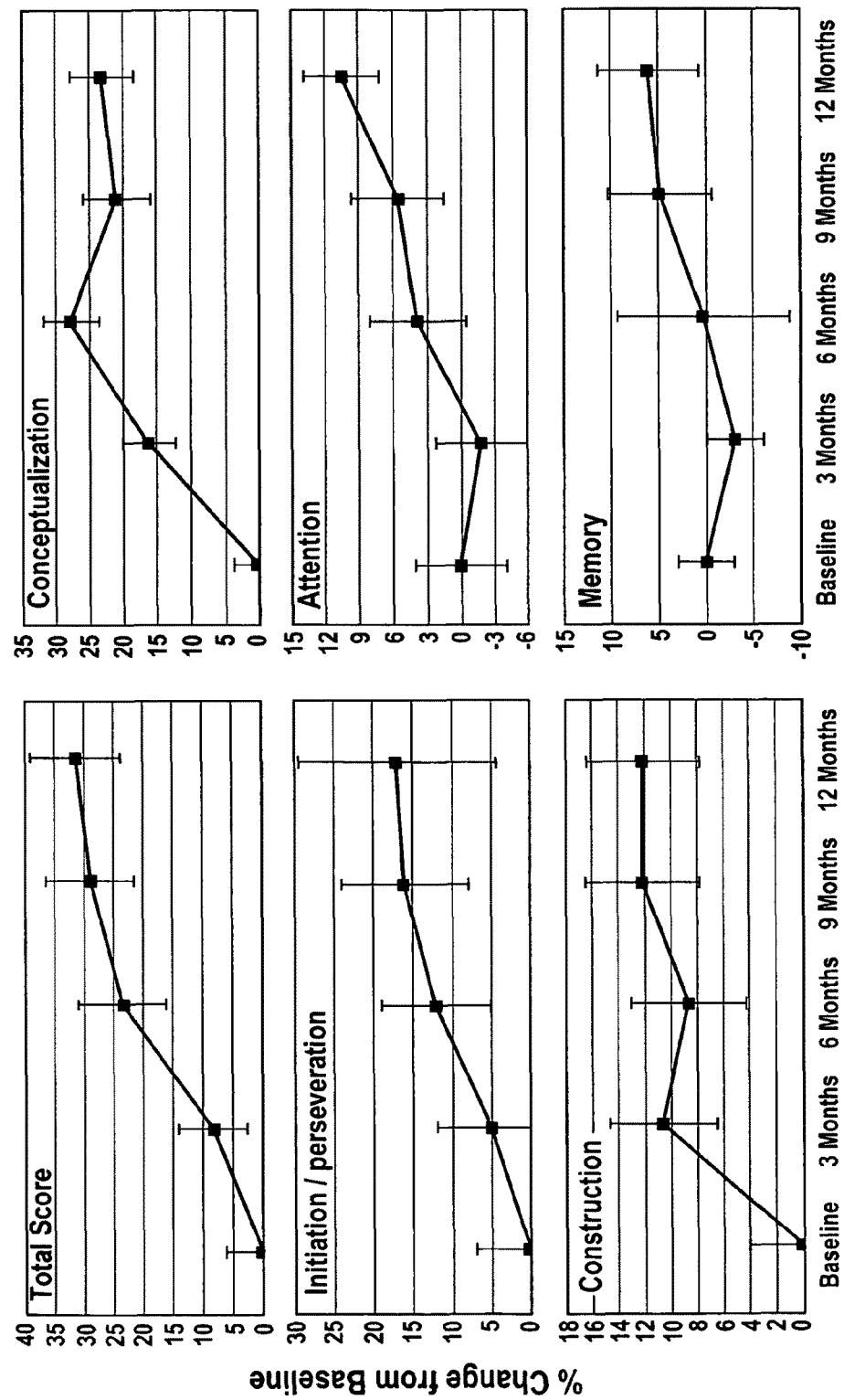
FIG. 6 graphically depicts improvement in cognitive performance in patients diagnosed with early-stage Alzheimer's disease receiving Formulation A, as measured by the Dementia Rating Scale. Values in each panel represent mean raw scores for the total participants±the standard error of the mean; mean baseline scores were subtracted from all values to generate a baseline of zero.
Figure 7:
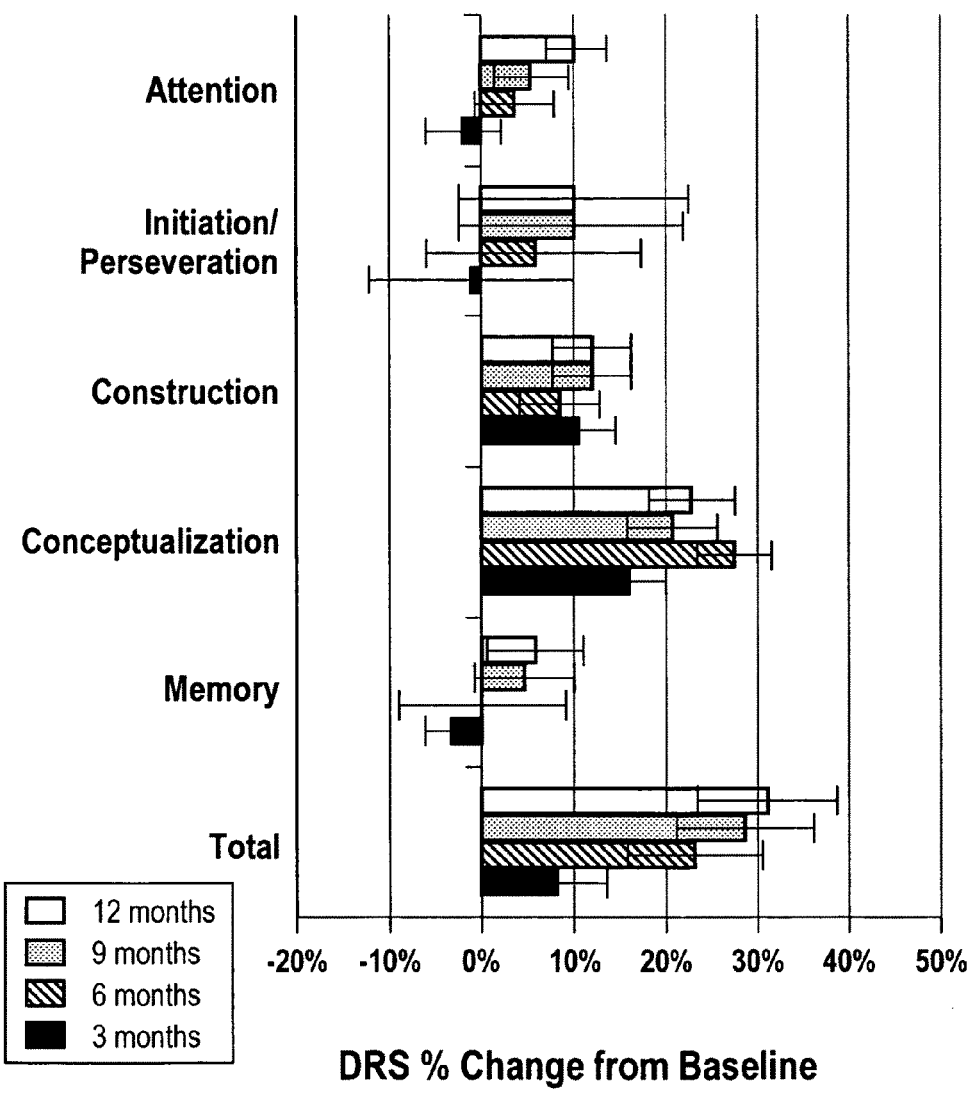
FIG. 7 graphically depicts the mean percentage change in scaled scores from baseline in each of the five domains assessed by the Dementia Rating Scale in patients diagnosed with Alzheimer's disease receiving Formulation A.

The DRS quantifies understanding, ability to complete a task, and attention. Patient tests demonstrated marked improvement within 3-6 months of receiving Formulation A in the DRS test, and maintenance of this improvement for at least 12 months, as shown in FIG. 6. Specifically, participants demonstrated statistical improvement (p<0.02) within 6 months in total performance on the DRS, with a trend towards statistical improvement (p<0.06) by 3 months. Participants maintained statistical improvement until 12 months, with an overall improvement of 31±8% (mean±standard error) at 12 months. A clinically-significant effect size for total performance was achieved within 3 months and was maintained for the duration of this trial (Table 1). Varying responses were observed for individual categories of this test (see FIGS. 6 and 7). A statistically-significant improvement in conceptualization (p<0.01) and construction (p<0.03) was observed within 3 months and was maintained for the duration of the study. A trend (p<0.06) toward statistical significance in initiation/ perseveration was observed within 9 months; statistical significance was achieved by 12 months (p<0.04). A significant difference in attention (p<0.01) was first observed at 12 months. No significant difference in memory (p<0.18) was observed by 12 months, although limited improvement, with no evidence of decline was observed in this category (FIG. 6).

Figure 8:
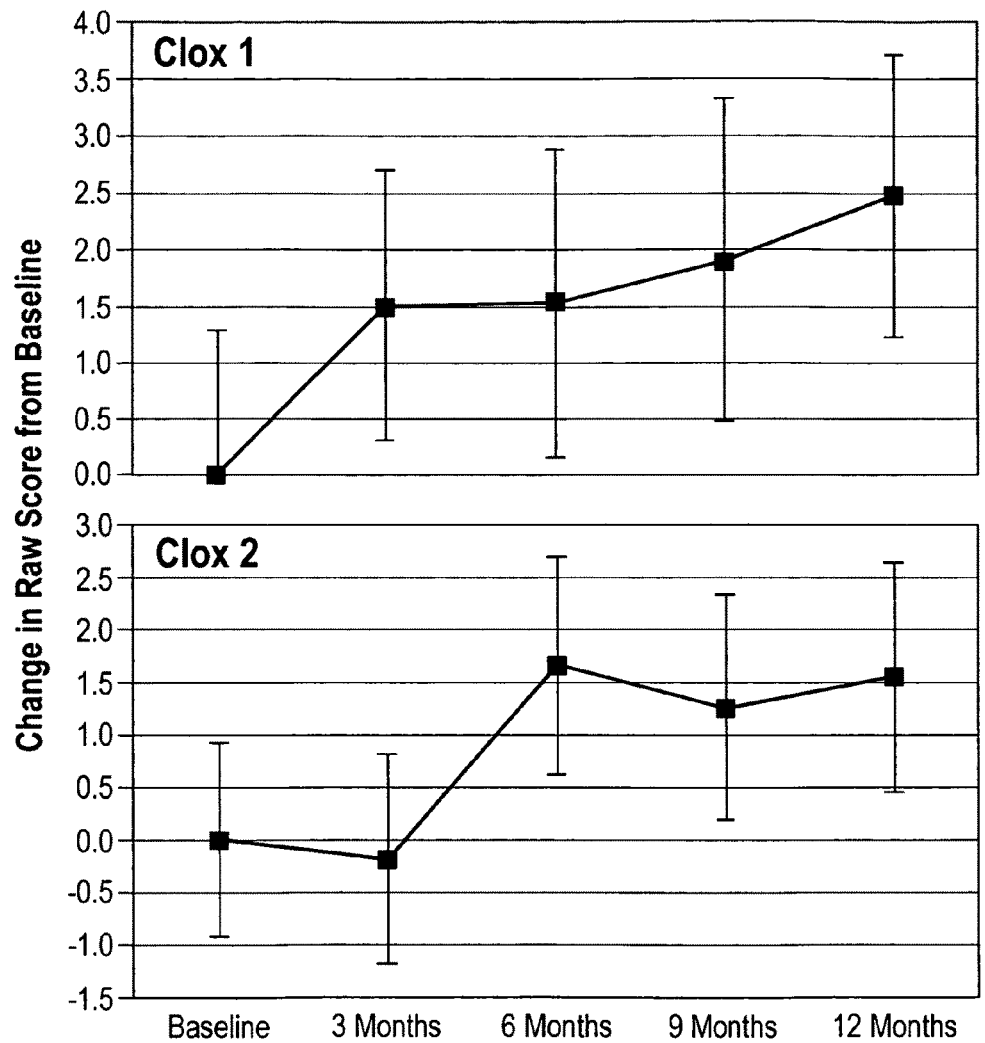
FIG. 8 graphically depicts improvement in cognitive performance in patients diagnosed with early-stage Alzheimer's disease receiving Formulation A, as measured by clock-drawing tests Clox 1 and Clox 2. Values in each panel represent mean total scores for the total participants±the standard error of the mean; mean baseline scores were subtracted from all values to generate a baseline of zero.

Participants were also administered the Clox Drawing test as an additional measure of cognitive performance. Clox 1, which asks subjects to draw a clock indicating a specified time on a blank sheet of paper, serves as a measure of executive function. Clox 2 asks subjects to copy a clock drawn by the examiner. These two tests are thought to reflect the specific contribution of executive control versus visuospatial performance, respectively. Participants demonstrated a progressive increase, although not statistically significant, in performance in both Clox 1 and 2 over the 12-month trial (p<0.08 and p<0.18, 12 months vs. baseline, respectively; see FIG. 8). Clinical significance was achieved within 3 months for Clox 1 and 6 months for Clox 2, and was maintained for both tests over the duration of the trial (Table 1).

Figure 9A:
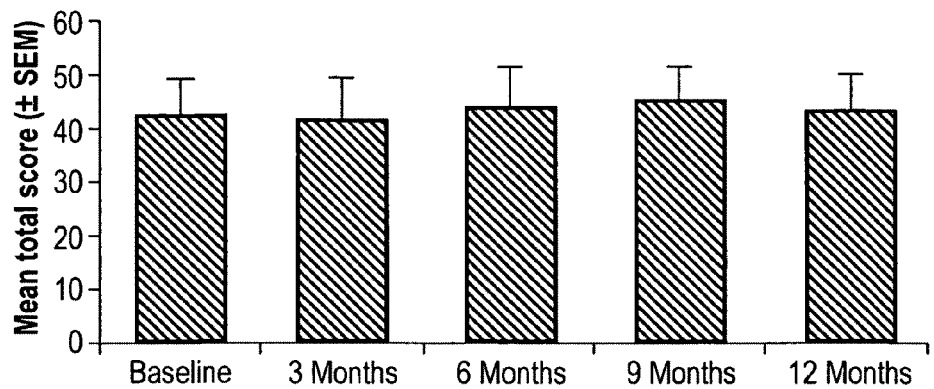
FIG. 9 graphically depicts maintenance in the ability to carry out daily activities among early-stage Alzheimer's Disease patients receiving Formulation A over 1 year (FIG. 9A) and 18 months (FIG. 9B), as measured by the Activities of Daily Living scale. The graphs presents total scores (mean±standard error) in ADCS-ADL as reported by caregivers.
FIG. 9B contains ADCS-ADL scores for only the subset of participants (7) that continued receiving Formulation A for 6 months following the initial 12 month trial.
Figure 9B:
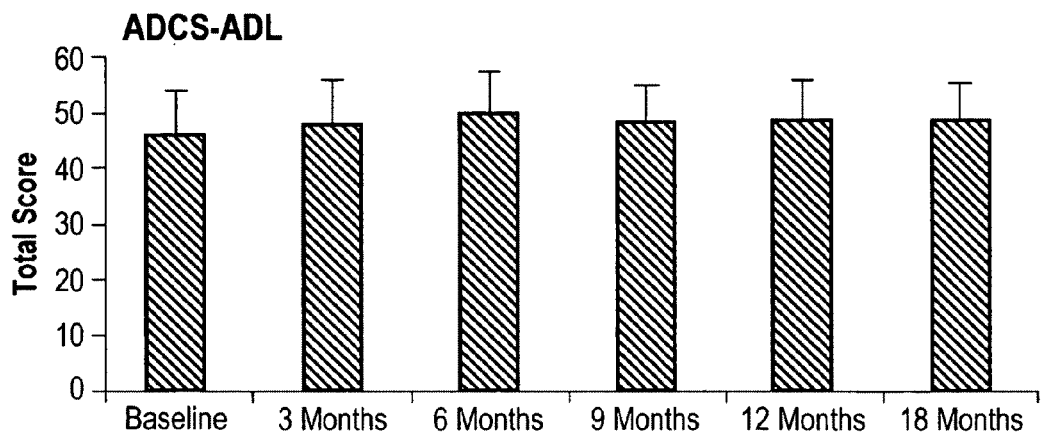

Caregiver reports also demonstrated maintenance of functions measured by the Activities of Daily Living scale, as shown in FIG. 9A. Scores are based upon the ability and degree to which an individual is able to engage in daily tasks, including those that demonstrate autonomy, simple motor skills, higher level functions, and basic activities (e.g., ability to utilize appliances and telephone, dress oneself, maintain hygiene, etc.). Participants demonstrated no mean change in their ability to carry out the day-to-day functions quantified by this test over the year-long trial (see FIG. 6). Importantly, no mean decline was witnessed. Varying responses were observed among participants in this caregiver test; 6/14 participants demonstrated an increased score (8.8±1.9, mean±standard deviation), 3 demonstrated no change, and the remaining 5 declined (−8.2±6.7, mean±standard deviation). A subset (7) of these caregivers supplied ADCS-ADL information for their family members at 18 months, which revealed sustained levels of performance comparable to those observed at 12 months (FIG. 9B).

The trial described herein illustrates that after 12 months of taking Formulation A, participants' cognitive skills not only improved, but this improvement was maintained throughout the course of the study. This study further indicates that Formulation A was safe and well-tolerated in patients with Alzheimer's Disease. In conclusion, the data presented here demonstrate a role for Formulation A as a low-cost, over-the-counter neuroprotectant that may maintain neuronal health prior to dementia, and delay the decline associated with Alzheimer's Disease.

TABLE 1

Effect size of Formulation A

|  | 3 months | 6 months | 9 months | 12 months |
|---|---|---|---|---|
| DRS | 0.35 | 1.17** | 1.57** | 1.66** |
| NPI | 0.36 | 0.38 | 0.52 | 0.35 |
| Clox 1 | 0.28 | 0.29 | 0.38 | 0.47 |
| Clox 2 | 0** | 0.44 | 0.33 | 0.41 |

Values were calculated using raw scores at each time interval according to the formula: (mean at treatment time) − (mean at baseline)/standard deviation of baseline (Cohen, 1988). A single asterisk denotes large clinical significance (e.g., >0.8), while all unlabeled values were clinically significant (>.2; Cohen, 1988); the single double asterisk denotes non-significance. Note that clinical significance was achieved for DRS, NPI and Clox 1 within 3 months, and for Clox 2 within 6 months. Note further that large clinical significance was achieved for 6-12 months for DRS.

Example 4

Figure 10:
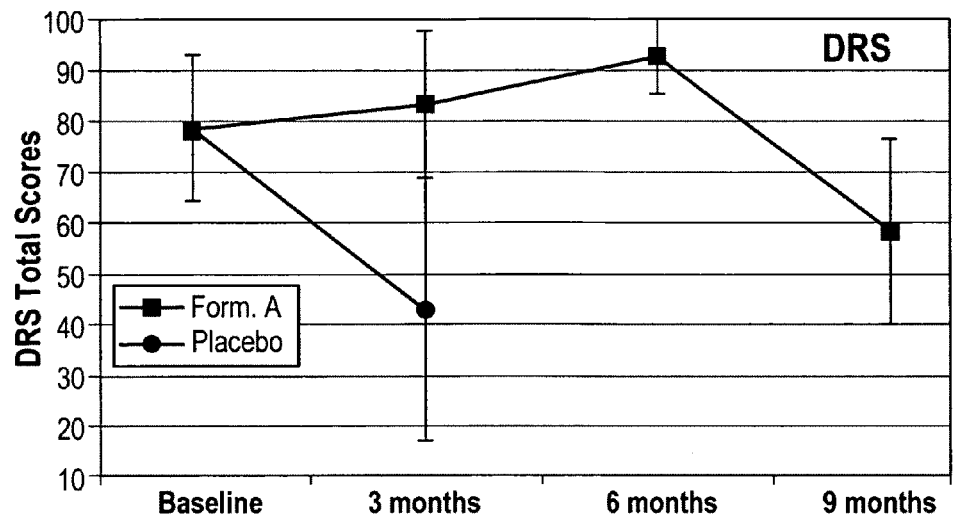
FIG. 10 graphically depicts improvement in cognitive performance in patients diagnosed with mid/late-stage Alzheimer's disease receiving Formulation A, as measured by the Dementia Rating Scale.
Figure 11:
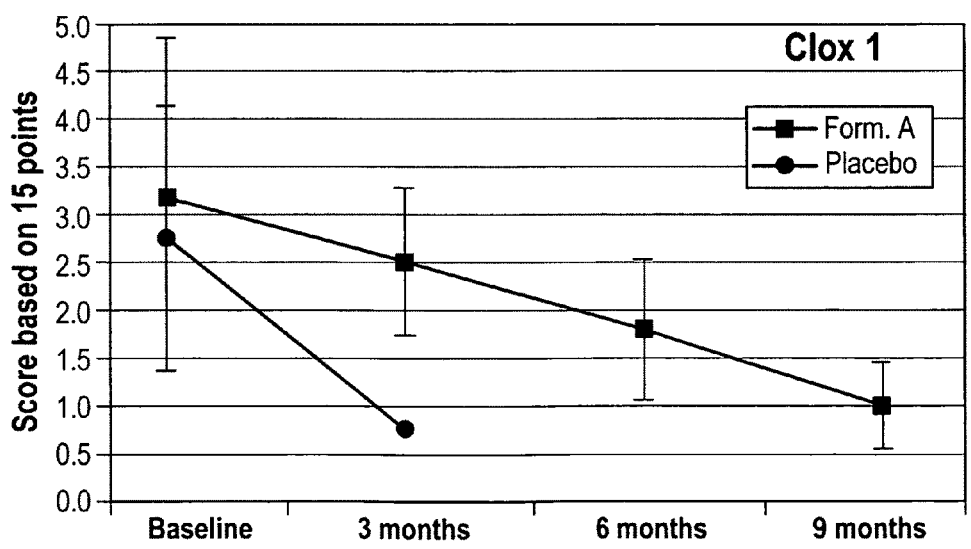
FIG. 11 depicts improvement in cognitive performance in patients diagnosed with Mid/Late-Stage Alzheimer's Disease receiving Formulation A, as measured by Clox 1 performance.

Improvement in Cognitive Performance in Adults Diagnosed with Mid/Late Stage Alzheimer's Disease Ten participants (Nursing home residents) with mid- to late-stage Alzheimer's disease received Formulation A (n=6) or placebo (n=4) for 3 months. The degree of AD in these patients was considered moderate to severe (MMSE scores of 11.9±2.5). Formulation A contained the following components: folate at a dosage of about 2-10 μg/kg, vitamin E at a dosage of about 0.2-0.7 IU/kg, vitamin B12 at a dosage of about 0.04-0.14 μg/kg, N-acetyl cysteine at a dosage of about 4-14 mg/kg, acetyl-L-carnitine at a dosage of about 3-12 mg/kg, and S-adenosyl methionine at a dosage of about 3-10 mg/kg. As shown in FIG. 10, participants receiving Formulation A demonstrated improvement in the Dementia Rating Scale (DRS), while individuals receiving placebo declined. Formulation A also delayed the decline in Clox 1 vs. placebo, as shown in FIG. 11 (Clox 1 is a cognitige neuropsychological test commonly used to measure executive control function in AD patients). Clinical significance (0.9 and 0.38) was attained for Formulation A at 3 months in DRS and Clox 1, respectively. Two participants withdrew from the Formulation A group at 6 months, and all but one participant withdrew from the placebo group (this individual is not represented at 6 and 9 months in FIGS. 10 and 11). Participants withdrew due to difficulty consuming tablets; one placebo-group individual's dementia progressed to the point of cessation of all medication. These results indicate that Formula A improves cognition in patients diagnosed with late-stage Alzheimer's Disease, and support the usefulness of Formulation A in treating late-stage AD.

Example 5

Improvement in Mood and Behavior in Adults Diagnosed with Early Stage Alzheimer's Disease The objective of the study described herein was to examine the effect of a nutriceutical formulation on mood and behavior in patients with early-stage Alzheimer's Disease. An open-label trial was conducted in which eighteen early-stage free-living Alzheimer patients received Formulation A, containing folate at a dosage of about 2-10 μg/kg, vitamin E at a dosage of about 0.2-0.7 IU/kg, vitamin B12 at a dosage of about 0.04-0.14 μg/kg, N-acetyl cysteine at a dosage of about 4-14 mg/kg, acetyl-L-carnitine at a dosage of about 3-12 mg/kg, and S-adenosyl methionine at a dosage of about 3-10 mg/kg. Patients received 2 capsules daily, each containing a combination of 400 ug of folic acid, 6 ug of Vitamin B12, 30 IU Vitamin E (as alpha-tocopherol), 400 mg of S-adenosylmethionine, 600 mg of N-acetyl cysteine, and 500 mg of Acetyl-L-carnitine. The study design is outlined in FIG. 5, and is also described in Example 3. Inclusion criteria were as follows: (1) clinical diagnosis of early-stage AD (according to the NINCDS criteria for probable AD; 61), (2) ≥50 years of age, (3) no history or diagnosis of Bipolar Disorder (since SAM is contraindicated for bipolar disorder; 42), and (4) ineffectiveness of and/or adverse events with certain prescribed AD pharmaceuticals. DRS-II scores normalized for age and education level characterized participants as having mild to moderate AD (Mattis Dementia Rating Scale; 62). Participants were asked to maintain their normal dietary regimen and vitamin/medication intake throughout the course of this study. Although not a specified inclusion criterion, all participants had at least one family member caregiver who provided evaluations. Participants and caregivers were informed that they would receive NF for 12 months, and could elect for continued participation beyond 12 months, and that only serious adverse events, rather than lack of efficacy, could prompt exclusion from the study.

A family caregiver completed the Neuropsychiatric Inventory (NPI) for each patient. The NPI is a 12-item survey which quantifies mood, irritability, attention, etc., and determines the degree to which abnormal behavior affects a patient's well-being. The same caregiver reported at each time interval.

Figure 12:
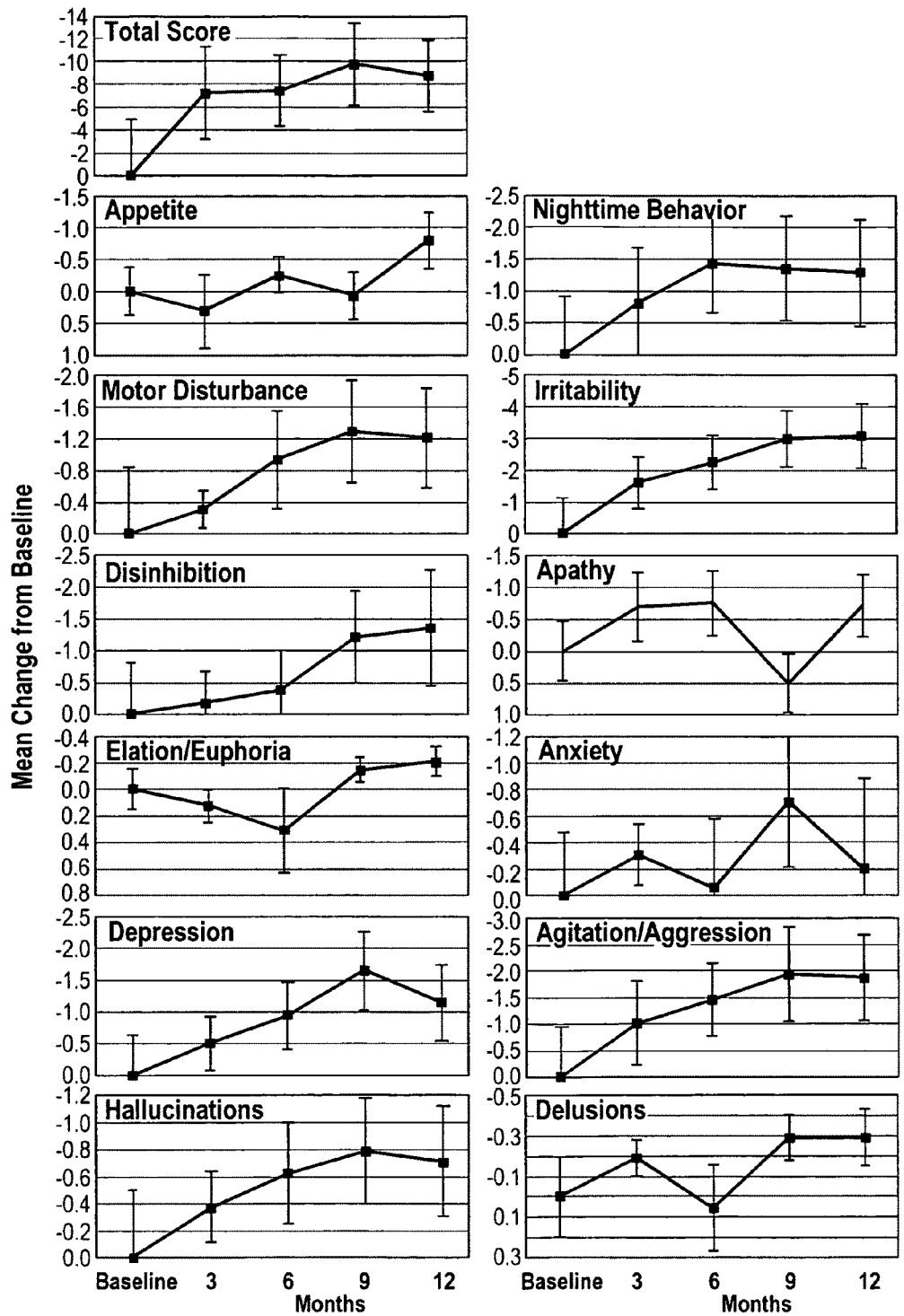
FIG. 12 graphically depicts improvement in mood, irritability, and attention in patients diagnosed with early-stage Alzheimer's disease receiving Formulation A over 1 year, as measured by the Neuropsychiatric Inventory (NPI). Values in each panel represent mean raw scores for the total number of participants+the standard error of the mean; for presentation of "Total Score," mean baseline scores were subtracted from all values to generate a baseline of zero. Since a decrease in score denotes improvement, the y axes have been inverted for clarity.
Figure 13:
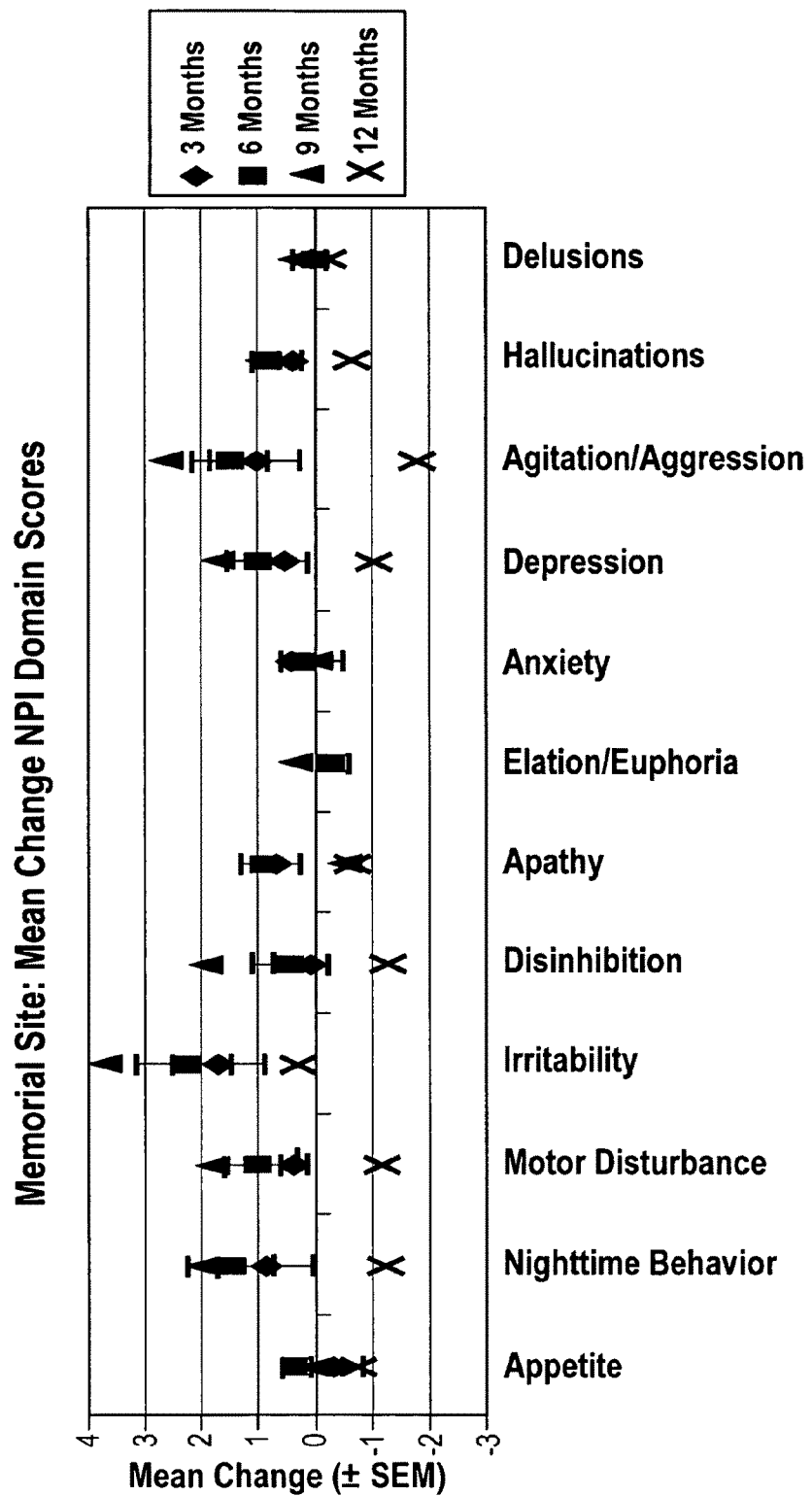
FIG. 13 depicts the mean change in scores from baseline for each of the 12 behaviors assessed by the NPI in patients diagnosed with early-stage Alzheimer's Disease receiving Formulation A for 1 year.
Figure 14:
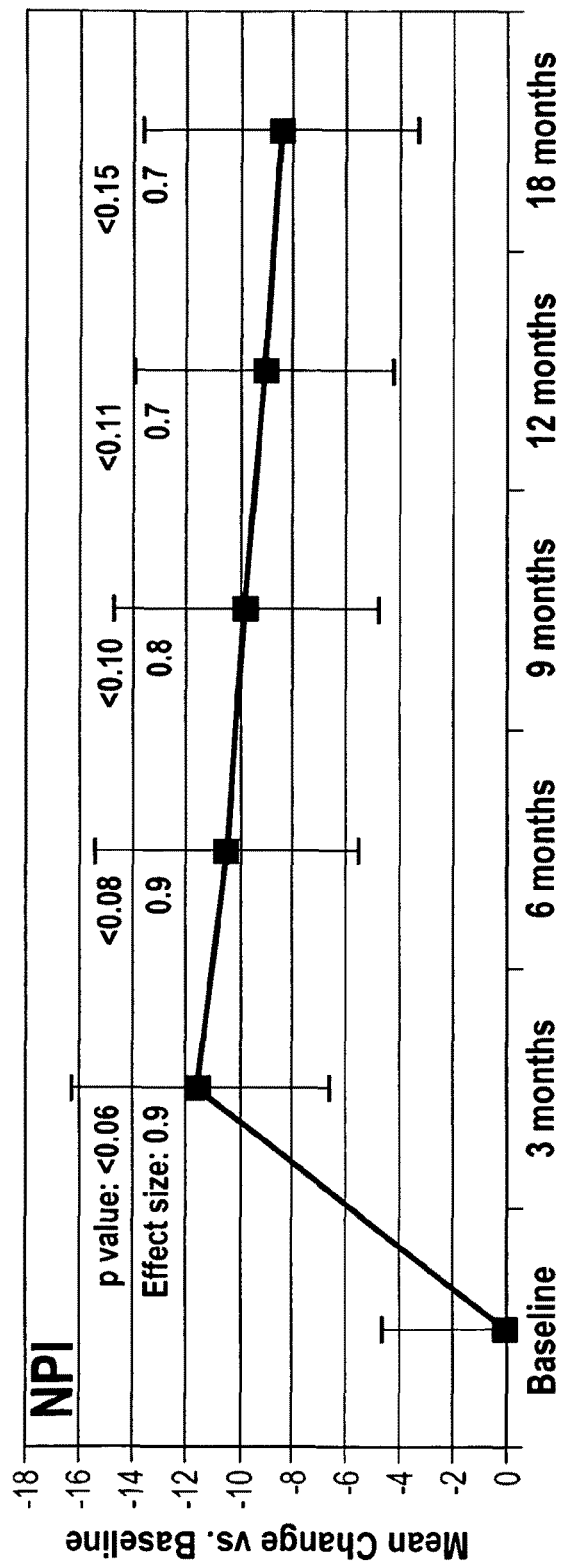
FIG. 14 depicts improvement in mood, irritability, and attention in patients diagnosed with early-stage Alzheimer's disease receiving Formulation A over 18 months, as measured by the Neuropsychiatric Inventory (NPI). NPI scores (mean total score±standard error) are presented from baseline to 18 months for the subset of participants (7) that continued receiving Formulation A for 6 months following the initial 12 month trial. P values and effect size are noted at each time point; these are diminished as compared to the starting population due to the smaller participant number in this subset (7 vs. 14).

Mean changes in NPI scores from study initiation to completion are illustrated in FIG. 12. Scores are based on the presence of 12 abnormal behaviors most commonly associated with dementia, the severity of these behaviors, and the degree of distress experienced by caregivers. In the case of this outcome measure, a lower score indicates clinical improvement, i.e., the behaviors are present to a lesser degree, and do not cause as much distress. As a decreased score denotes improvement, the y axes depicted in FIG. 12 have been inverted for clarity. Participants demonstrated marked improvement in total NPI score within 3 months of receiving Formulation A, and maintained this improvement for at least 12 months, as shown in FIG. 12. A trend towards significance ($p<0.07$) was observed for the total score at 3 months; significant improvement ($p<0.02$) was observed at 6 months, and was maintained until 12 months ($p<0.001$). Formulation A had the maximum effect on the irritability and agitation/aggression domains of the NPI. A significant improvement ($p<0.03$) in aggression was observed at 6 months; significance was maintained until 12 months ($p<0.05$). A trend towards significance was observed for motor performance at 3 months and for depression at 6 months ($p<0.07$, each) and were each maintained as such until 12 months. The remaining parameters did not demonstate statistical change; however, none showed a decline over 12 months (FIG. 12). Notably these latter domains were markedly less evident at baseline, precluding evaluation of NF efficacy in these domains for the total participant population. However, one participant had baseline evaluations of 6, 4 and 2 for Hallucinations, Apathy and Appetite, respectively, but by 12 months these domains were evaluated at 0. Another participant declined from 6 to 4 for Hallucinations over 12 months, another declined from 4 to 2 for Apathy and 2 to 1 for Appetite, and a third declined from 2 to 0 for Appetite. The extent of improvement for these participants in these individual domains rivals or exceeds the overall efficacy observed for irritability and agitation/aggression, underscoring that Formulation A is apparently effective for a wider range of domains than is revealed by this study. It remains possible that Formulation A may have delayed manifestation of behavioral issues over the course of the 12-month trial for those not exhibiting these behavioral problems at baseline. On average, caregivers reported that patients engaged in less abnormal behavior over the course of the year-long trial. There was a general trend of improvement across several behaviors, most notably in aggression and irritability, as shown in FIGS. 12 and 13. A subset (7) of these caregivers supplied NPI results for their family members at 18 months, which revealed sustained levels of performance comparable to those observed at 12 months (FIG. 14). A significant effect size (>0.8) was achieved within 3 months and was maintained for the duration of this trial (Table 1).

Figure 15:
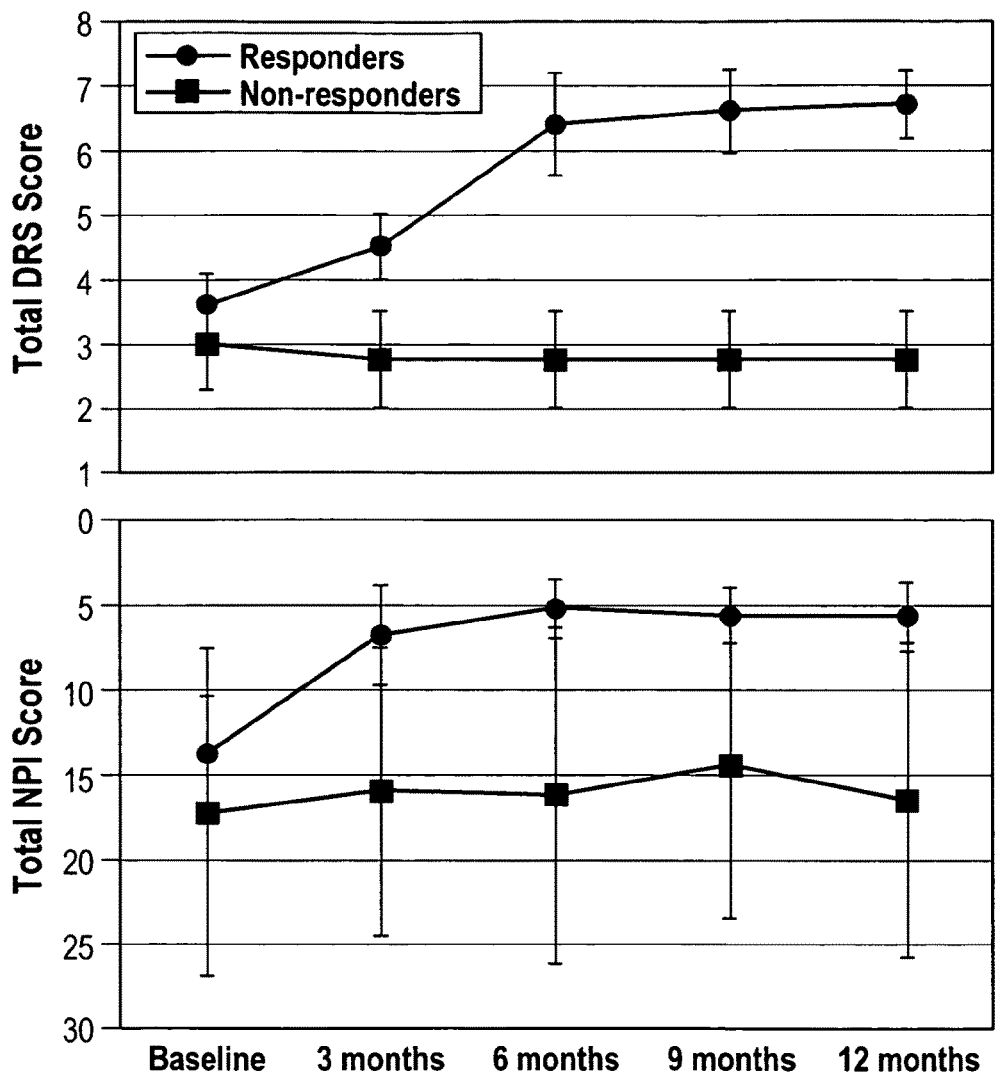
FIG. 15 depicts the correlation between performance in DRS and performance in NPI. Graphs present the mean±standard error of participant scores in DRS and NPI following grouping into responders or non-responders according to DRS performance. As a decline in NPI score constitutes improvement, the Y axis of the NPI graph is inverted to facilitate comparison between DRS and NPI.

To determine whether or not caregiver reports correlated with participant performance, the correlation between participant performance in the DRS (as described in Example 3) and respective caregiver reports in the NPI was examined. To accomplish this, participants were classified as "responders" if their total DRS score at 12 months exceeded that at baseline, and "non-responders" if their total score at 12 months remained the same or declined versus baseline. Over the 12-month trial, 10/14 participants improved in DRS scores, 2 participants displayed no change, and 2 individuals declined slightly. The individuals demonstrating improved scores were defined as responders, and the remaining 4 individuals were defined as non-responders (Table 2; see also FIG. 15). Slight but non-significant differences were observed in mean baseline scores for responders and nonresponders. The respective NPI scores for these participants were then examined, and participants who demonstrated a decline in total NPI scores at 12 months vs. baseline were defined as NPI responders (note: a decline in NPI indicates improvement). A comparison between DRS scores and NPI scores revealed that DRS performance was highly correlated with NPI performance. 8/10 DRS responders were also NPI responders, and 2/4 of DRS non-responders were also NPI non-responders. Identical results were obtained when participants were first grouped according to NPI performance: 8/10 NPI responders were also DRS responders, and 2/2 NPI non-responders were also DRS non-responders (Table 2). Since these are independent tests, one of which is completed by the participant without caregiver input, and the other completed by the caregiver without participant input, there is no inherent reason to anticipate correlation of test results above that of chance (i.e., 50%). The observed correlation of 10/14 participant scores for these independent tests (71%) provides internal support for test validity. We noted a much wider error range for NPI non-responders than for responders; the standard error was approx 60% of the mean over all time points, while that of responders was only approx 30% (Table 2; FIG. 15). When taken together, the results described herein indicate that Formulation A improves detrimental behavior characteristic of Alzheimer patients, and specifically improves mood and reduces irritability and aggression in patients diagnosed with early-stage Alzheimer's disease.

Figure 16:
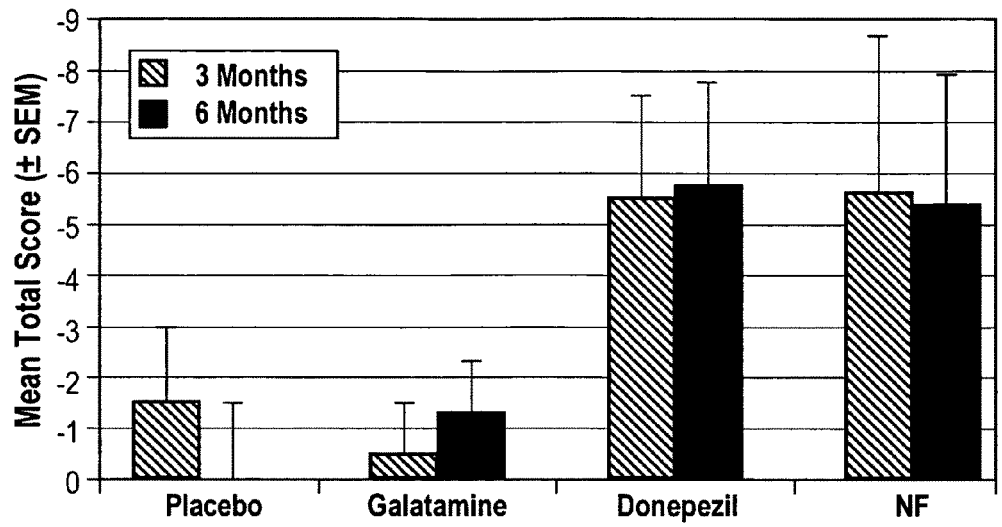
FIG. 16 presents a comparison of the efficacy of Formulation A with that of Donepezil, Galantamine, and their respective placebo groups. Total NPI scores of participants from the study described herein following 3 months and 6 months of treatment with Formulation A are compared with those from published studies for galantamine and donepezil, and with the averaged scores from the placebo groups of both studies.
Figure 17:
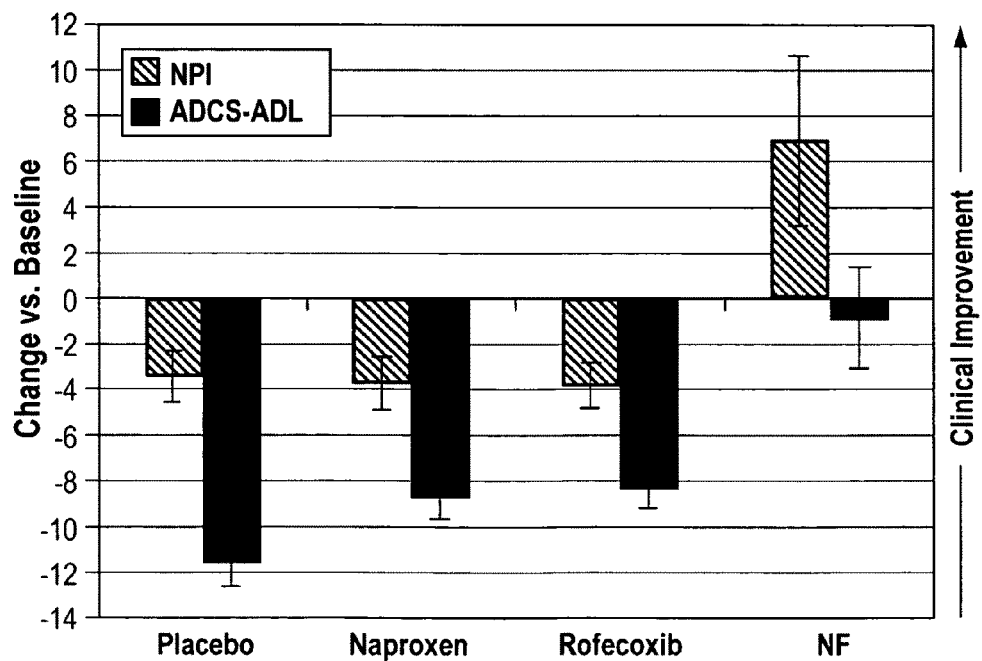
FIG. 17 presents a comparison of the efficacy of Formulation A with that of naproxen, rofecoxib, and their respective placebo groups. Total NPI and ADCS-ADL scores of participants from the study described herein following 12 months of treatment with Formulation A are compared with those from a prior study where participants received naproxen (n=118), rofecoxib (n=122) or placebo (n=111) for 12 months. Positive values correspond to improvement; negative values correspond to decline.

The NPI and ADCS-ADL scores of early-stage Alzheimer's patients following administration of Formulation A (described above and in Example 3) were compared with those obtained in previous studies of various pharmacological agents and their respective placebo groups. This comparison indicated that patients administered Formulation A performed equally well in the NPI as did individuals receiving donepezil, and far exceeded the performance of individuals receiving galantamine or placebo over 3-6 months (as reported by Erkinjuntti et al., (2002) Lancet 359:1283-1290 and Feldman et al., (2001) Neurology 57:613-620; comparison is presented in FIG. 16). In addition, patients receiving Formulation A demonstrated superior performance over 12 months in both the NPI and the ADCS-ADL with respect to individuals receiving the anti-inflammatory agents naproxen and rofecoxib, or their respective placebo groups (as reported by Aisen et al., (2003) JAMA 289:2819-2826; comparison is presented in FIG. 17). Neither naproxen nor rofecoxib statistically improved performance on the NPI, nor prevented decline in ADCS-ADL; however a trend towards diminished decline was observed (p<10.5 and 9.7 vs. placebo, respectively). According to this comparison, individuals receiving Formulation A markedly exceeded the performance of those receiving either drug or placebo in both NPI and ADCS-ADL.

TABLE 2

Total DRS scores of Responders and Non-responders

| | Baseline | 3 months | 6 months | 9 months | 12 months |
|---|---|---|---|---|---|
| Total DRS Score of Responders* | | | | | |
| Participant** | | | | | |
| 1 | 2 | 2 | 2 | 3 | 5 |
| 2 | 6 | 7 | 9 | 9 | 9 |
| 3 | 3 | 4 | 5 | 6 | 6 |
| 4 | 3 | 5 | 9 | 9 | 9 |
| 5 | 5 | 6 | 8 | 8 | 7 |
| 6 | 2 | 5 | 6 | 6 | 6 |
| 7 | 2 | 2 | 3 | 4 | 4 |
| 8 | 5 | 5 | 9 | 7 | 7 |
| 9 | 5 | 5 | 7 | 8 | 8 |
| 10 | 3 | 4 | 6 | 6 | 6 |
| Mean ± SEM | 3.6 ± 0.5 | 4.5 ± 0.5 | 6.4 ± 0.8 | 6.6 ± 0.6 | 6.7 ± 0.5 |
| P value*** | — | 0.13 | 0.02 | 0.00 | 0.00 |
| Total DRS Score of Non-responders | | | | | |
| Participant | | | | | |
| 11 | 3 | 2 | 2 | 2 | 2 |
| 12 | 2 | 2 | 2 | 2 | 2 |
| 13 | 2 | 2 | 2 | 2 | 2 |
| 14 | 5 | 5 | 5 | 5 | 5 |
| Mean ± SEM | 3.0 ± 0.7 | 2.8 ± 0.8 | 2.8 ± 0.8 | 2.8 ± 0.8 | 2.8 ± 0.8 |
| P value | — | 0.81 | 0.81 | 0.81 | 0.81 |
| Total NPI Score**** | | | | | |
| Participant | | | | | |
| 1 | 1 | 0 | 0 | 0 | 1 |
| 2 | 2 | 4 | 2 | 0 | 0 |
| 3 | 19 | 3 | 15 | 5 | 17 |

TABLE 2-continued

Total DRS scores of Responders and Non-responders

|  | Baseline | 3 months | 6 months | 9 months | 12 months |
|---|---|---|---|---|---|
| 4 | 39 | 1 | 0 | 4 | 2 |
| 5 | 13 | 8 | 8 | 9 | 5 |
| 6 | 12 | 6 | 3 | 4 | 2 |
| 7 | 8 | 32 | 14 | 14 | 15 |
| 8 | 18 | 7 | 6 | 5 | 12 |
| 9 | 18 | 1 | 2 | 1 | 1 |
| 10 | 8 | 6 | 2 | 14 | 2 |
| Mean ± SEM | 13.8 ± 3.4 | 6.8 ± 2.9 | 5.2 ± 1.7 | 5.6 ± 1.6 | 5.7 ± 2.0 |
| P value | — | 0.23 | 0.06 | 0.07 | 0.07 |
| Total NPI Score*** | | | | | |
| Participant | | | | | |
| 11 | 1 | 0 | 0 | 0 | 0 |
| 12 | 1 | 3 | 4 | 4 | 6 |
| 13 | 28 | 27 | 17 | 14 | 18 |
| 14 | 39 | 34 | 44 | 40 | 42 |
| Mean ± SEM | 17.3 ± 9.6 | 16.0 ± 8.5 | 16.3 ± 9.9 | 14.5 ± 9.0 | 16.5 ± 9.3 |
| P value | — | 0.93 | 0.94 | 0.84 | 0.96 |

Participants were classified as "responders" if their total DRS score at 12 months exceeded that at baseline, and "non-responders if their total score at 12 months remained the same or declined versus baseline. The mean ± standard error was calculated for responders and non-responders at each time point and statistically compared to baseline. The respective NPI scores for these participants were then examined; participants who demonstrated a decline in total NPI scores at 12 months vs. baseline were defined as NPI responders (note: a decline in NPI constitutes improvement; see Materials and Methods).
Note that 8/10 DRS responders were also NPI responders, and 2/4 of DRS non-responders were also NPI non-responders.
*Values represent raw total scores for DRS and NPI; participants sorted according to responders and non-responders as described in Methods
**arbitrary code numbers assigned for this table only; numbers refer to same participants in both DRS and NPI tabulations
***2-tailed Student's t test vs. baseline score Example 6

Figure 18:
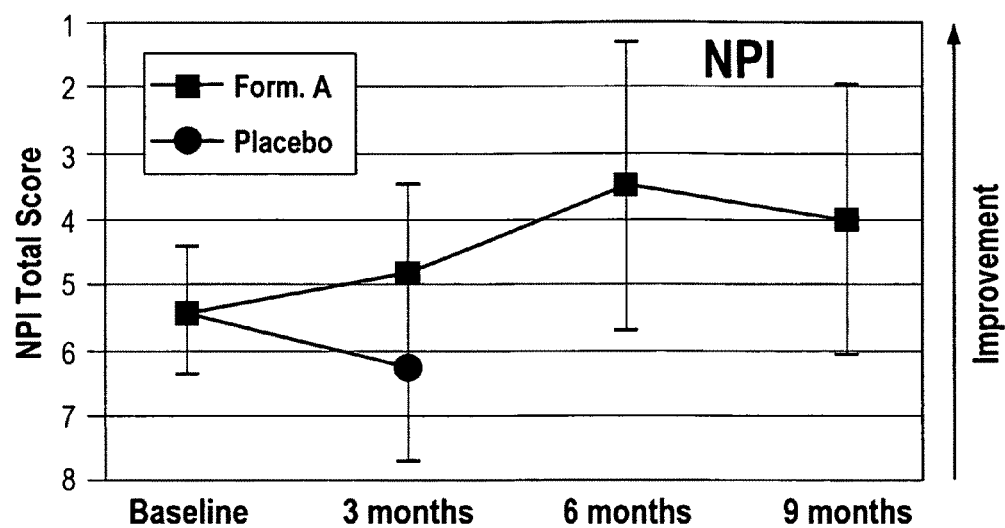
FIG. 18 graphically depicts improvement in mood, irritability, and attention in patients diagnosed with mid/late-stage Alzheimer's disease receiving Formulation A, as measured by the Neuropsychiatric Inventory (NPI).
Figure 19:
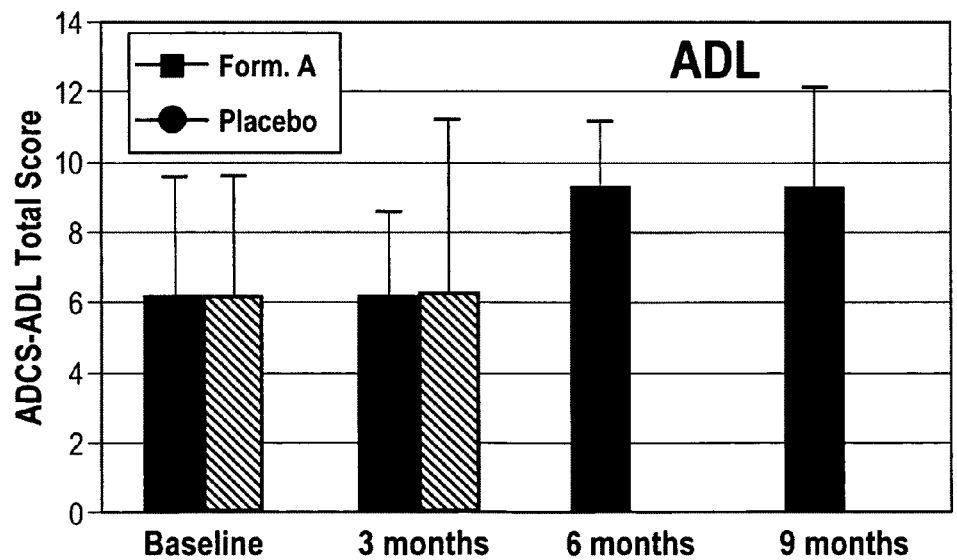
FIG. 19 graphically depicts maintenance in the ability to carry out daily activities in patients diagnosed with Mid/Late-Stage Alzheimer's Disease receiving Formulation A, as measured by the Activities of Daily Living Scale (ADCS-ADL)

Improvement in Mood and Behavior in Adults Diagnosed with Mid/Late Stage Alzheimer's Disease Ten participants (Nursing home residents) with mid- to late-stage Alzheimer's disease received Formulation A (n=6) or placebo (n=4) for 3 months. The degree of AD in these patients was considered moderate to severe (MMSE scores of 11.9±2.5). Formulation A contained the following components: folate at a dosage of about 2-10 μg/kg, vitamin E at a dosage of about 0.2-0.7 IU/kg, vitamin B12 at a dosage of about 0.04-0.14 μg/kg, N-acetyl cysteine at a dosage of about 4-14 mg/kg, acetyl-L-carnitine at a dosage of about 3-12 mg/kg, and S-adenosyl methionine at a dosage of about 3-10 mg/kg. As shown in FIG. 12, participants receiving Formulation A demonstrated improvement in the Neuropsychiatric Inventory (NPI), which quantifies mood, irritability, attention, etc., while individuals receiving placebo declined. Institutional caregivers also reported that participants receiving Formulation A maintained performance on the ADCS-ADL (described above; results are depicted in FIG. 19). Two participants withdrew from the Formulation A group at 6 months, and all but one participant withdrew from the placebo group (this individual is not represented at 6 and 9 months in FIGS. 18 and 19). Participants withdrew due to difficulty consuming tablets; one placebo-group individual's dementia progressed to the point of cessation of all medication. These results indicate that Formulation A improves mood and reduces irritability in patients diagnosed with mid/late-stage Alzheimer's disease.

Example 7

Effect of Dietary Supplementation with N-Acetyl Cysteine, Acetyl-L-Carnitine and S-Adenosyl Methionine on Cognitive Performance and Aggression in Mice expressing Human ApoE4

The objective of the study described herein was to examine the efficacy of a nutriceutical formulation on cognitive performance in mice expressing human ApoE4, a mouse model of Alzheimer's Disease. Groups of normal C57B/6 mice, and mice of the same genetic background but expressing human ApoE4 (n=8 in 2 independent experiments, 9-12 months of age) received a standard AIN-76 diet (Purina/Mother Hubbard, Inc.), or the same diet but lacking folate and vitamin E, and supplemented with iron (50 g/500 g total diet) as a pro-oxidant (defined as the "deficient diet") for 2 weeks to 1 month. Additional groups received these diets supplemented with a combination of N-acetyl cysteine (NAC, 5 g/kg total wet weight of diet); acetyl-L-carnitine (ALCAR, 1 g/kg diet); and S-adenosylmethionine (SAM, 100 mg/kg). These dietary supplements are proposed to act in multiple biological pathways. For example, NAC is an antioxidant and glutathione precursor that buffers Abeta neurotoxicity and prevents cognitive decline, ALCAR raises ATP levels, protects neuronal mitochondria, buffers Abeta neurotoxicity and supports cognitive performance, and SAM facilitates glutathione usage, reduces oxidative damage to brain tissue, prevents cognitive decline and maintains acetylcholine levels.

Cognitive impairment was monitored using a standard Y maze test as described (Chan et al., 2006; Mihalik et al., 2003). The pattern of exploration of the Y maze was recorded over 5 min intervals for each mouse. The frequency in which mice visited each of the 3 arms in succession during any 3-arm visitation sequence versus the total visitations defines the "% alternation."

The "resident intruder test," was utilized to quantify the frequency and severity of aggressive behavior (Kumar-Singh et al, 2000). In this isolation-induced aggression test, "resident" male non-transgenic and transgenic mice (9-12 months of age at the time of testing) were housed solitarily for one week prior to testing. "Intruders" were randomly selected from a population of non-transgenic male C57/B16 mice, 9-12 months of age at the time of testing, that had been housed in groups of four since weaning. Aggression of the resident was quantified by measuring the latency before the first attack by the resident following introduction of an intruder and the number of attacks during a 3-min session once the attacks had initiated; an "attack" was defined as biting, tail rattling, aggressive grooming, charging, and/or butting of the intruder. The following day, the same resident mice were tested a second time with different intruders.

Mice were sequentially maintained on complete or deficient diets, with and without supplementation with NAC, ALCAR and SAM, and subjected to Y maze tests and aggression tests at the end of each interval. Performance in the Y maze tests and aggression tests for various diets were statistically compared to "starting" values obtained for the respective mice (i.e., maintained on the complete diet) via Student's t test.

Figure 20:
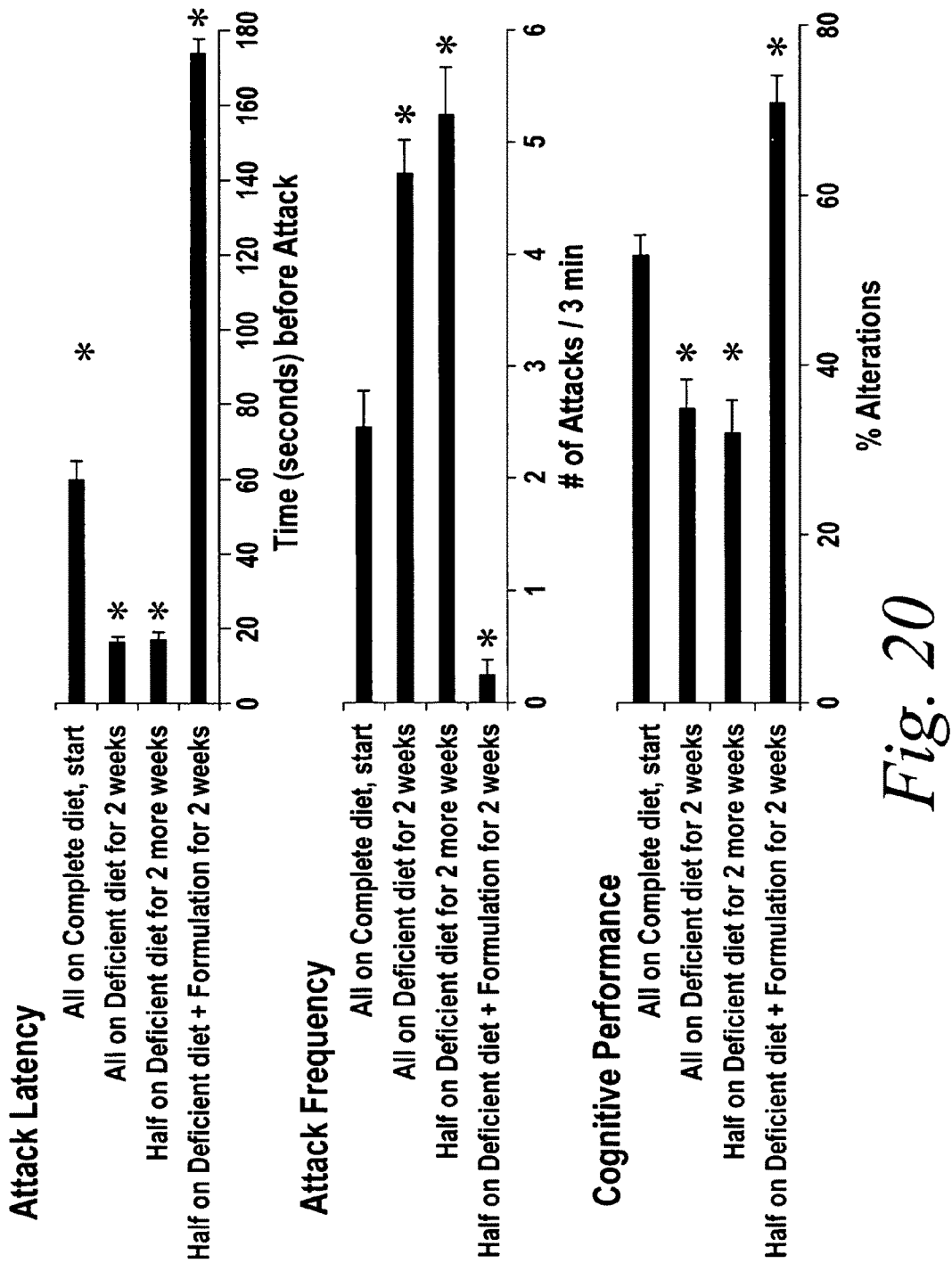
FIG. 20 depicts improvement in cognitive performance and reduction in aggression following dietary supplementation with NAC, ALCAR, and SAM in ApoE4 mice. Transgenic mice expressing ApoE4 (n=6 in 2 independent experiments) maintained on the complete diet were subjected to intruder-based aggression and Y maze analyses. All mice were then switched to the deficient diet and tested again after two weeks. Half of these mice were maintained on the deficient diet for an additional two weeks, while the other half instead received the deficient diet supplemented with NAC, ALCAR and SAM ("formulation") for 2 weeks, after which they were tested for a third time. A decline in attack latency, an increase in attack frequency, and a decline in cognitive performance was seen within 2 weeks of maintenance on the deficient diet. Following maintenance on the deficient diet supplemented with NAC, ALCAR, and SAM, the increase in attack latency, decline in attack frequency and increase in cognitive performance beyond that of baseline levels. Values represent the mean±standard error recorded for all mice in both experiments; values accompanied by an asterisk differed statistically from values obtained for mice on the complete diet ("start").

Transgenic mice expressing ApoE4 displayed varying degrees of aggression under all dietary conditions utilized herein. When maintained on a complete diet, mice expressing ApoE4 displayed a latency of approx. 1 min prior to the first attack on an intruder, and then attacked the intruder an average of 2.5 times in 3 min, as shown in FIG. 20. Latency was reduced by approx. 30%, and the frequency of attacks approximately doubled within two weeks of maintenance of these mice on the deficient diet (see FIG. 20). These altered levels remained unchanged for mice maintained on the deficient diet an additional 2 weeks. In contrast, when the deficient diet was supplemented with NAC, ALCAR and SAM for these latter 2 weeks, attack latency increased approximately 90% and attack frequency declined by approx. 95%, as shown in FIG. 20. These latter values represent approximately a 30% increase in latency and a 90% decrease in frequency versus the original starting values for these mice. Performance in the Y maze was likewise affected by supplementation with NAC, ALCAR and SAM. Maintenance of mice expressing ApoE4 on the deficient diet resulted in an approximate 30% decline in cognitive performance within 2 weeks, while supplementation of the deficient diet with NAC, ALCAR and SAM increased cognitive performance approximately 30% beyond the original starting values for these mice, as shown in FIG. 20.

These results demonstrate that combined treatment with NAC, ALCAR, and SAM prevents the decline in cognitive performance and increase in aggression associated with mice expressing the human E4 allele of ApoE. In addition to their benefit on cognition and aggression, NAC, ALCAR and SAM each reduce oxidative damage to brain tissue. NAC and SAM accomplish this via increasing levels and efficacy of glutathione (De La Cruz et al., 2002; Dhitavat et al., 2001; Farr et al., 2003; Fu et al., 2006; Ho et al., 2003; Tchantchou et al., 2004, 2005a,b; Vilalobos et al., 2000), while ALCAR supports mitochondrial activity (Barnes et al., 1990; Dhitavat et al., 2001, 2002, 2005; Markowska and Olton, 1990). Differential mechanisms for buffering oxidative stress suggest that the combination of these agents will exert superior antioxidant protection versus any one agent. The findings of the present study suggest that supplementation with NAC, ALCAR and SAM may exert multiple neuroprotective effects in patients with Alzheimer's disease, resulting in improved cognitive function and reduced aggression.

Example 8

Folate Deprivation Increases Presenilin Expression, Gamma-secretase Activity, and Abeta levels in Murine Brain: Potentiation by ApoE Deficiency and Alleviation by Dietary S-Adenosyl Methionine Folate deprivation promotes age-related neurodegenerative disorders including Alzheimer's disease (AD; Mattson and Shea, (2003) Trends Neurosci. 26:137-146). Folate deficiency fosters a decline in S-adenosyl methionine (SAM; the major methyl donor), decreasing DNA methylation during aging and AD and increasing DNA breakage (Kruman et al., (2002) J. Neurosci. 22:1752-1762). Folate deficiency and resultant SAM depletion potentiate several AD genetic risk factors. These include increasing homocysteine, which potentiates Abeta-induced oxidative damage (Ho et al., (2003) Neurobiol. Dis. 14:32-42; White et al., (2001) J. Neurochem. 76:1509-1520), while simultaneously compromising glutathione usage, which further increases oxidative stress and potentiates the impact of ApoE deficiency (Kamboch et al., (2004) Hum. Biol. 67:195-215; Tchantchou et al., (2005) J. Nutr. Health Aging 10:541-544). SAM declines, while its hydrolysis product S-adenosyl homocysteine (SAH) increases in AD; SAH inhibits methyl transferases that utilize SAM and therefore further inhibits SAM-dependent methylation in AD. Since SAM regulates neurotransmitter levels including that of acetylcholine (Albert et al., (2000) Nutrition 16:544-581; Chan et al., (2007) in press; Miscouloun and Fava, (2002) Am. J. Clin. Nutr. 76:1158S-1161S), the decline in SAM that accompanies folate deprivation is likely to underlie the cognitive decline and increased aggression observed in mice deprived of dietary folate and/or genetically compromised in folate usage (Chan et al., (2006) Mol. Neurodegener. 1:8).

A major genetic risk factor for AD is the presence of the E4 allele of apolipoprotein E (ApoE; Growdon, (2001) J. Alzheimers Dis. 3:287-292). Oxidative damage in the brain is elevated in AD patients, and the extent of this damage correlates with the presence of the E4 allele (Ramassamy et al., (1999) Free Radic. Biol. Med. 27:544-553). Transgenic mice lacking ApoE ("ApoE–/– mice") exhibit increased oxidative stress, and, while not equivalent to the consequences of expression of E4, represent a useful model for the impact of oxidative stress on neurodegeneration (e.g., Huang et al., (2000) Life Sci. 68:19-28; Ramassamy et al., (1999) Free Radic. Biol. Med. 27:544-553; Shea and Rogers, (2002) Mol. Brain. Res. 108:1-6; Shea et al., (2002) Free Radic. Biol. Med. 33:1115-1120; Shea et al., (2002) J. Alzheimers Dis. 4: 1-6). ApoE–/– mice exhibit increased susceptibility to folate deprivation: within 1 month of folate deprivation, ApoE–/– mice, but not normal mice, display oxidative damage in brain tissue in a gene-dose manner, impaired cognitive performance (Mihalick et al., (2004) Neuromol. Med. 4:197-202; Shea and Rogers, (2002) Mol. Brain. Res. 108:1-6; Shea et al., (2002) Free Radic. Biol. Med. 33:1115-1120; Shea et al., (2002) J. Alzheimers Dis. 4: 1-6; Tchantchou et al., (2004) J. Neurosci. Res. 75:508; Tchantchou et al., (2005) J. Alzheimers Dis. 7:135-138; Tchantchou (2006) Nutr. Neurosci. 9:17-24; Tchantchou (2006) J. Nutr. Health Aging 10:541-544). Brain tissue of ApoE–/– mice contains markedly reduced SAM, and that this critical reduction is further augmented by folate deficiency, leading to a block in quenching of oxidative species by glutathione (GSH), a decline in ACH, and an increase in levels of phospho-tau. Synergistic interactions of folate deprivation and known risk factors for AD such as Abeta exposure (Ho et al., (2001) J. Neurochem. 78:249-53; Ho et al, (2003) Neurobiol. Dis. 14:32-42; White et al., (2001) J. Neurochem. 76:1509-1520) and ApoE deficiency (Kruman et al., (2002) J. Neurosci. 22:1752-1762) can promote neurodegeneration under conditions in which neither agent alone exhibited detectable impact. These latter considerations underscore the importance of investigating the impact of folate deficiency on additional risk factors for neurodegeneration. Recent studies in culture indicate that overexpression of presenilin-1 (PS-1) and a resultant increase in Abeta generation, both major hallmarks of AD (Brunkan and Goate, (2005) J. Neurochem. 93:769-792), are downstream consequences of folate deprivation that can be alleviated by supplementation of folate-deficient culture medium with SAM (Fuso et al., (2005) Mol. Cell. Neurosci. 28:195-204).

One objective of the study described herein was to determine whether or not dietary folate deprivation and SAM supplementation could exert similar effects in murine brain. A second objective was to determine whether or not any increases in PS-1 and Abeta were potentiated by ApoE deficiency, since ApoE deficiency not only potentiates other deleterious consequences of folate deprivation (above), but can also augment the deleterious consequences of PS-1 overexpression (Pastor et al., (2003) Ann. Neurol. 54:163-169) and impair clearance of Abeta (Cam and Bu, (2006) Mol. Neurodegener. 1:8; Fagan et al., (2002) Neurobiol. Dis. 9:305-318; Hone et al., (2003) J. Alzheimers Dis. 5:1-8; Irizarry et al., (2004) J. Neurochem. 90:1132-1143; Manelli et al., (2006) Neurobiol. Aging; Trommer et al., (2005) Neurobiol. Dis. 18:75-82). A third objective was to examine the activity of gamma secretase under these conditions, since activity of this enzyme, which generates Abeta, is increased by PS-1 overexpression as well as ApoE deficiency (Irizarry e al., (2004) J. Neurochem. 90:1132-1143; Pastor et al., (2003) Ann. Neurol. 54:163-169).

Adult (9-12 months of age) C57B/6 mice that either express ("normal") or lack murine ApoE (ApoE−/− mice) received a diet ("AIN-76"; Purina/Mother Hubbard, Inc.) either lacking folate and vitamin E (defined as the "deficient diet") or supplemented with folic acid (4 mg/kg), and vitamin E (50 IU/kg total diet wet weight) (defined as the "complete diet"). The deficient diet was also supplemented in all cases with iron (50 g/500 g total diet) as a pro-oxidant (Mihalick et al., (2004) Neuromol. Med. 4:197-202; Shea and Rogers, (2002) Mol. Brain. Res. 108:1-6). Additional groups of mice maintained on each diet received SAM for the entire month (100 mg/kg diet; Chan et al., (2007) in press; Tchantchou et al., (2005) J. Alzheimers Dis. 7:135-138). Following 1 month of maintenance on these diets, mice were sacrificed by cervical dislocation, and the frontal portion of the brain (encompassing cortex and hippocampus) was immediately removed.

To analyze PS-1 expression, total mRNA was extracted from the above homogenate using an RNA isolation kit and stored at −20° C. as described (Chan and Shea, (2006) J. Alzheimers Dis. 9:399-405). Transcription of murine PS-1 was analyzed using a set of primers 5'-ACGGTTTCCAACATCCATCG-3' (SEQ ID NO: 1) and 5'-GATGACAGGGACTGTTGAGCAA-3' (SEQ ID NO: 2) respectively, which yielded a product of 557 base pairs (bp) of the murine PS-1 gene. As in our prior studies, the "housekeeping gene" glyceraldehyde phosphate dehydrogenase (GADPH), used as a normalization factor, was amplified using the primers 5'-ACCACAGTCCATGCCATCAC-3' (SEQ ID NO: 3), and 5'-TCCACCACCCTGTTGCTGTA-3' (SEQ ID NO: 4) respectively, which yielded a product of 451 bp. Sequences were verified using the BLAST algorithm function (available on the GeneBank website). RT-PCR was carried out in a single tube using the Access RT-PCR kit (Promega, Calif.). As per the manufacturer's recommendation, 2 μg (in 3 μl) of purified mRNA and 0.5 mM each of forward and reverse primers were used in each reaction, with amplification for 35 cycles (Tchantchou et al., (2004) J. Neurosci. Res. 75:508). RT-PCR products were electrophoresed on a 2% agarose gel, containing ethidium bromide at 0.2 mg/ml (90 V for 1 hour). Gels were visualized under UV using a Gel Doc 2000 machine from BioRad and analyzed using Quantity One software. The 557 bp and 451 bp products were eluted from the gel, cloned, and verified as PS-1 and GAPDH via sequencing on a Beckman/Coulter CEQ-200X using dye-terminator chemistry.

Gamma secretase activity was quantified by fluorescent spectroscopy using a gamma secretase activity kit according to the manufacturer's instructions (R&D Systems, Minneapolis, MN), using the APP peptide GVVIATVIV (SEQ ID NO: 5) conjugated to the reporter molecules EDANS and DABCYL and measuring the cleavage-dependent release of signal at 495 nm.

A portion (40-50 mg) of the above cortical/hippocampal sample was homogenized with 4 volumes of Tris-saline (50 mM Tris HCl, pH 7.4, 150 mM NaCl containing 1 mM EGTA, 0.5 mM diisopropyl fluorophosphate, 0.5 mM phenylmethylsulfonyl fluoride, 1 μg/ml N-p-tosyl-L-lysine chloromethylketone, 0.1 μg/ml pepstatin, 1 μg/ml antipain, and 1 μg/ml leupeptin). The homogenate was centrifuged at 500,000 RPM for 50 minutes at 4° C. Pellets were resuspended by brief sonication in 10 volumes of 6M guanidine HCl in 50 mM Tris-HCl, pH 7.6, followed by centrifugation at 450,000 RPM for 22 minutes at 4° C. The insoluble pellet was dilapidated with chloroform/methanol (2:1) and then with chloroform/methanol/water (1:2:0.8). The residue was extracted with 70% formic acid, and dried using a SpeedVac (Savant Instruments, Farmingdale, N.Y.). Replicate samples of the resulting pellet, normalized for protein content, were subjected to SDS-gel electrophoresis, transferred to PVDF membrane, and visualized by chemiluminescent reaction with anti-Abeta antibody BC05 (Morishima-Kawashima et al., 2000).

NIH Image software (v 1.62) was utilized to determine the density of the RT-PCR PS-1 and GADPH housekeeping gene and levels of Abeta. PS-1 expression was normalized for each sample according to GADPH expression using the formula [(PS-1 densitometric units/GADPH densitometric units)× PS-1 densitometric units)]. Statistical analyses were completed by using ANOVA with Fischer's PLSD (Chan et al., (2007) in press). Values were considered statistically significant if $p \leq 0.05$.

PS-1 is a polytopic membrane protein that is highly conserved and is expressed at low levels in essentially all cell types (Wines-Samuelson et al., (2005) Dev. Biol. 277:332-346). The physiological functions of PS-1 have not been fully characterized. Among the known functions of presenilin-1 are proper formation of the axial skeleton, as well as normal neurogenesis and neuron survival. Of critical importance, however, is that PS-1 is part of the gamma-secretase complex, and PS-1 overexpression will foster increased regulation of gamma-secretase activity, which in turn will increase generation of Abeta (Borchlet, (1998) Neurobiol. Aging 19:15-18; Fraser et al., (2001) Biochem. Soc. Symp. 67:89-100; Lee et al., (1996) J. Neurosci. 16:7513-7525). The results described herein demonstrate a critical potentiation of dietary and genetic predisposition on overexpression of normal PS-1, resulting in increased generation of Abeta.

Figure 21:
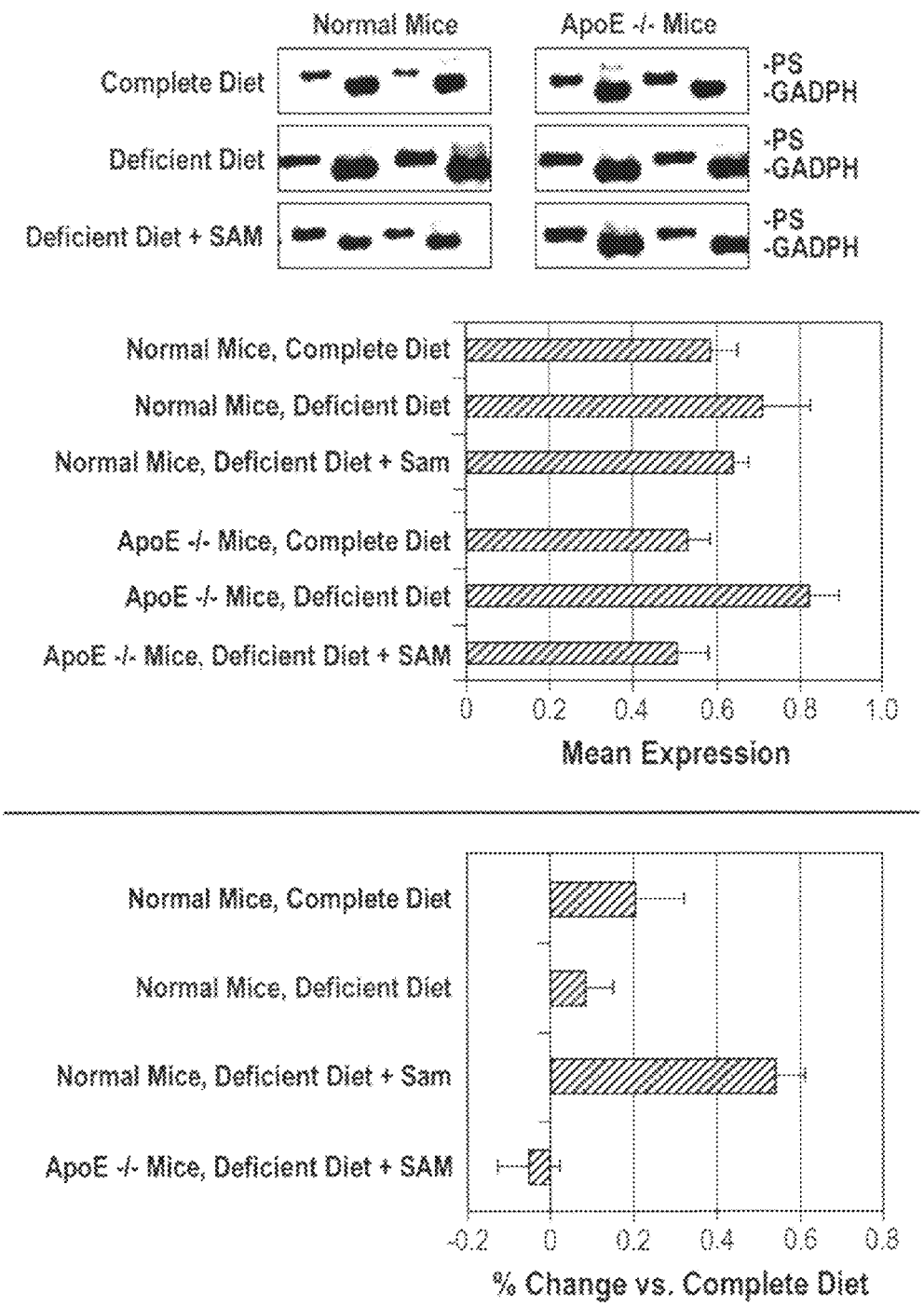
FIG. 21 depicts the increase in presenilin-1 (PS-1) expression following dietary folate and vitamin E deficiency coupled with iron challenge, and attenuation of this increase by S-adenosyl methionine (SAM). Panels present representative RT-PCR products generated from total mRNA of normal and ApoE−/− mice using primers for PS-1 and GADPH; two sets of samples for each mouse genotype are presented. The accompanying graphs present the mean increase±the standard error in PS-1 expression levels (normalized according to corresponding GADPH levels) for a total of 7-8 normal and 7-8 ApoE−/− mice of each age group on each indicated diet compiled from 2 separate experiments. The deficient diet significantly increased PS-1 expression in ApoE−/− mice (asterisk). Supplementation with SAM prevented or attenuated these increases, and in some cases reduced expression below that of normal mice on the complete diet.

Normal and ApoE−/− mice expressed similar levels of PS-1 when maintained on the complete diet, as shown in FIG. 21. However, maintenance on the deficient diet exerted a more severe affect on PS-1 expression in ApoE−/− mice than normal mice. Normal mice displayed an approx 20% increase when maintained on the deficient diet, while ApoE−/− mice displayed an approximate 50% increase (FIG. 21). Supplementation of this diet with SAM prevented these increases (FIG. 21).

Figure 22:
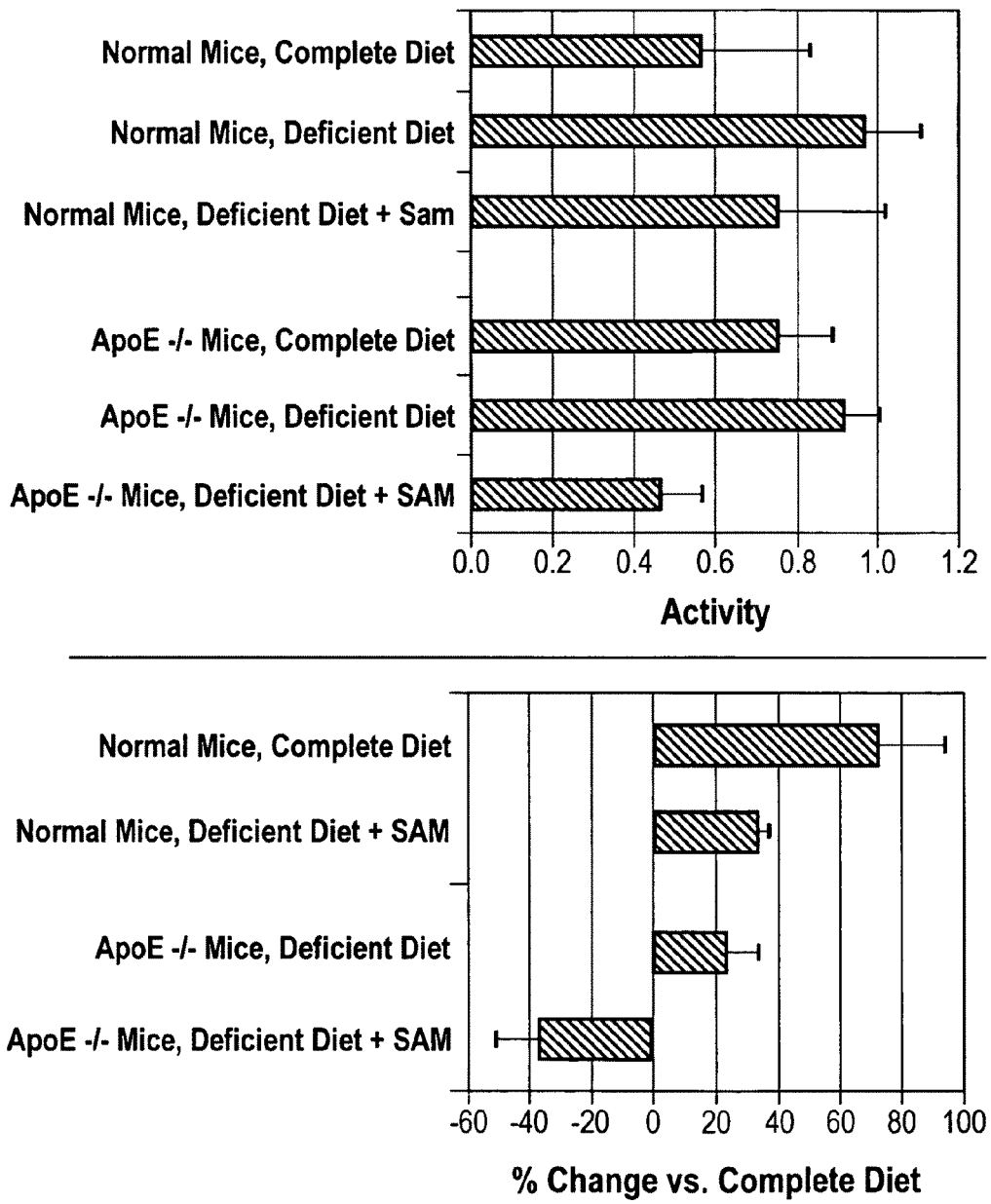
FIG. 22 depicts the increase in gamma-secretase activity following folate deprivation, and alleviation this increase by S-adenosyl methionine (SAM). Gamma-secretase activity was quantified in normalized homogenates from the same mice using a kit from R&D Biosciences according to the manufacturer's instruction. Folate deprivation significantly increased activity in normal mice (asterisk). Supplementation with SAM reduced secretase activity in normal mice (not statistically significant) and statistically ($p<0.02$) reduced secretase activity in ApoE−/− mice. Values were derived from a total of 7-8 normal and 7-8 ApoE−/− mice of each age group on each indicated diet compiled from 2 separate experiments.

Normal and ApoE−/− mice displayed different levels of gamma-secretase activity when maintained on the complete diet; ApoE−/− mice displayed 32±24% more activity than that of normal mice. Both genotypes displayed a further increase when maintained on the deficient diet. Activity increased beyond that observed on the complete diet by approx. 70% in normal mice, and approx. 20% in ApoE−/− mice. Supplementation of the deficient diet with SAM reduced these increases in both genotypes. The increase observed in normal mice maintained on the deficient diet was attenuated by half following SAM supplementation (to approx. 35% of that observed for these mice when maintained on the complete diet). Supplementation of the deficient diet with SAM had a larger effect on ApoE−/− mice, and decreased gamma-secretase activity in ApoE−/− mice to approx. 40% less than levels observed for these mice on complete diet. The extent of this latter reduction resulted in ApoE−/− secretase levels similar to those observed for normal mice maintained on the complete diet, as indicated in FIG. 22.

Figure 23:
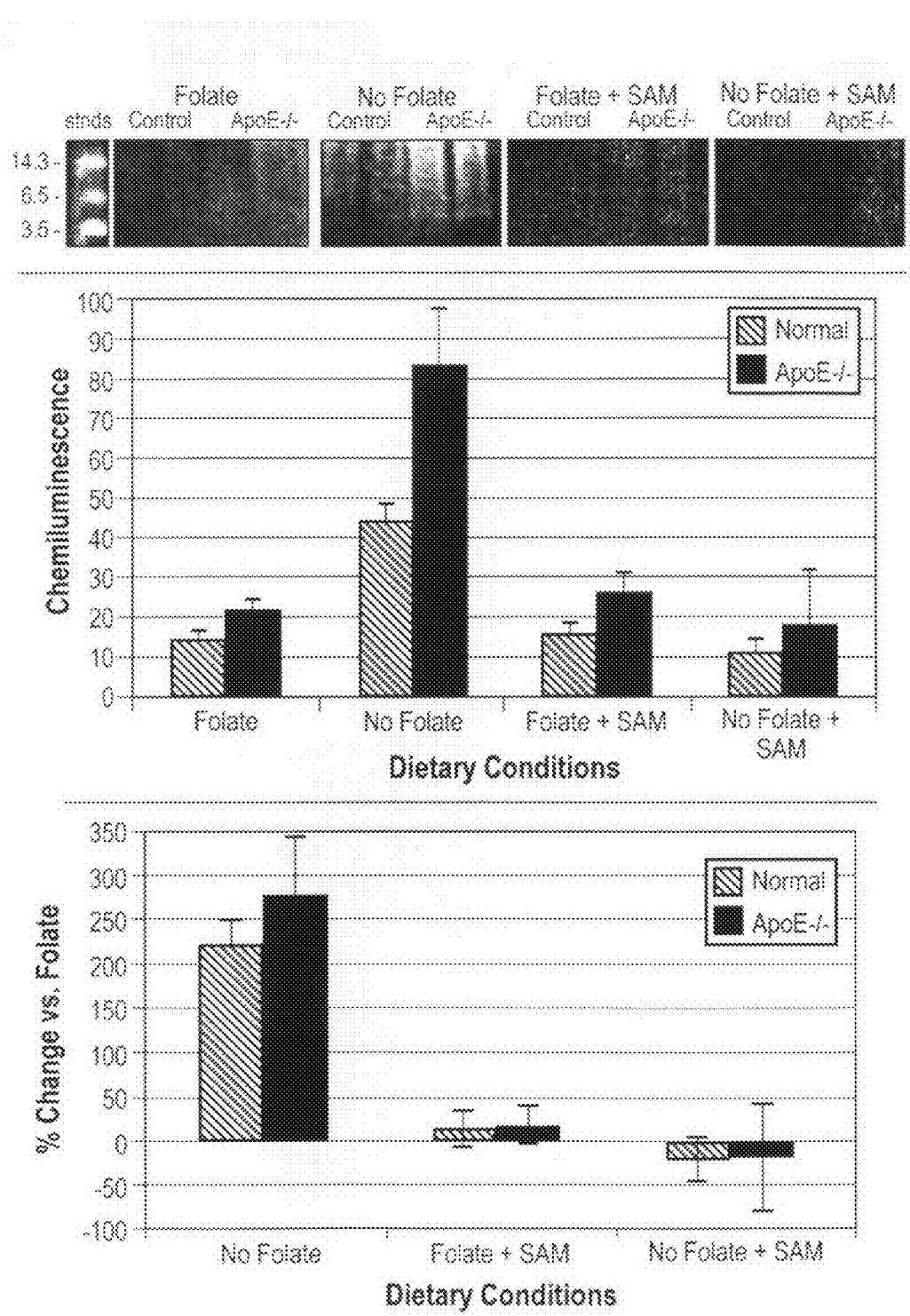
FIG. 23 depicts the increase in Abeta levels in ApoE−/− mice following folate deficiency, and prevention of this increase by supplementation with S-adenosyl methionine. Upper panels present samples from 2 normal and 2 ApoE−/− mice under each dietary condition as indicated. The 14.3-3.5 kDa region is presented. Note the presence of Abeta monomers at approx. 4 kDa; dimerization and further oligomerization is also observed. The accompanying graphs present the mean chemiluminiscent intensity (±standard deviation) of homogenates from 2 normal and 2 ApoE−/− mice from each of 2 experiments (total 4 mice of each genotype under each dietary condition), and the % change in chemiluminescence for normal and ApoE−/− mice under each dietary condition versus their respective genotype receiving the folate-supplemented diet. Folate deprivation fostered similar, significant relative increases in Abeta levels in both normal and ApoE−/− mice (asterisks), and that supplementation with SAM alleviated these increases.

Levels of Abeta were differentially affected in normal and ApoE−/− mice by dietary deficiency. Immunoblot analyses revealed Abeta monomers migrating at approx. 4 kDa, along with significant oligomerization, in both genotypes, as shown in FIG. 23. ApoE−/− mice displayed slightly more Abeta than normal mice when both were maintained on the complete diet. Folate deprivation increased Abeta levels in normal mice by over 200% and ApoE−/− mice by over 250% (p<0.2 and 0.3 vs. respective levels in the presence of folate). However, supplementation of the folate-deficient diet with SAM prevented these increases. Abeta levels for both genotypes receiving dietary SAM in the absence of folate were identical to those obtained with a folate-supplemented diet (p<0.5 and 0.7, respectively). Supplementation with SAM in the presence of folate did not alter values obtained with folate alone.

In conclusion, the study described herein examined the impact of a deficient diet on Abeta generation. The results indicate an increase in Abeta levels, as well as increases in PS-1 expression and gamma-secretase activity, both of which contribute to Abeta generation, when mice were maintained under this deficient diet for 1 month. Dietary and genetic compromise induced differential increases in PS-1 expression, gamma-secretase activity and Abeta levels in each mouse genotype. For example, normal and ApoE−/− mice displayed similar levels of PS-1 under the complete diet. By contrast, ApoE−/− mice displayed increased gamma-secretase activity, as well as increased Abeta levels, versus normal mice on the complete diet.

While both genotypes responded to the deficient diet by increasing PS-1 expression, gamma-secretase activity and Abeta levels, ApoE−/− mice displayed greater increases than those observed in normal mice, which is consistent with potentiation of the other consequences of this deficient diet by ApoE deficiency (above). These findings indicate that the combined impact of ApoE−/− deficiency, dietary deficiency in folate and vitamin E, and increased oxidative stress due to dietary iron consumption exert a greater deleterious impact than do these respective genetic or dietary deficiencies alone.

Potentiation of increased Abeta levels in ApoE−/− mice may also relate to deficient clearing of Abeta. It remains possible that a significant portion of the neurotoxicity resulting from folate deprivation, especially in combination with resultant Abeta accumulation, could be alleviated by antioxidant supplementation. However, the likelihood that SAM depletion is a key factor in the impact of the deficient diet as observed herein is supported by the alleviation or attenuation of the increases in PS-1 expression, gamma-secretase activity and Abeta levels following supplementation of the deficient diet with SAM. The overall reduced levels of SAM in ApoE−/− mice, coupled with the more severe reduction in SAM following dietary deficiency, is likely to contribute to the greater impact observed herein on PS-1 expression, gamma-secretase activity and Abeta levels observed in ApoE−/− versus normal mice. In this regard, SAM levels, and activity of the enzyme responsible for its generation (methionine-S-adenosyltransferase), are decreased in brain tissue of individuals exhibiting neurodegeneration (Bottiglieri et al. 1990; Gomes et al. 1994; Kennedy et al., 2004; Morrison et al. 1996; Muller et al., 2001). General antioxidant supplementation alone is unlikely to able to compensate for the full range of deleterious consequences of folate deprivation. These findings therefore underscore the potential usefulness of dietary supplementation with SAM as part of a therapeutic approach to minimize neurodegeneration.

The importance of dietary supplementation is underscored by the presence of critical thermolabile polymorphisms of 5,10-methylenetetrahydrofolate reductase (MTHFR), the enzyme required for the conversion of HC to methionine which uses folate as a cofactor, in as high as 20% of some populations (Brotto and Yang, 2000). Individuals homozygous for such polymorphisms variant exhibit mild hyperhomocysteinemia, which can remain latent, but is further augmented by diminished dietary folate (Chan et al., 2007; Frosst et al 1995; Shields et al., 1999) and linked to arterial disease and venous thrombosis (Arrula et al., 1997). Diminished activity of this enzyme also reduces production of tetrahydrofolate (required for DNA synthesis) and reduced adenosylmethionine (required for DNA methylation; Stern et al. 2000). MTHFR polymorphisms also impair neuronal development (O'Leary et al., 2005). Notably, a 36% increase in C677CT and A1298C polymorphisms has recently been reported among young people; such polymorphisms were present in 4.63% of individuals >24 yr of age, yet in 6.31% of those <24 yr of age (Reyes-Engel et al., 2002). The investigators considered that increased maternal dietary folate (confirmed in their samples) allowed an increase in fetal viability despite latent deficiencies in MTHFR. These data underscore an increased latency within the population of critical genetic deficiencies in folate metabolism that may manifest only with age-related nutritional decline. SAM supplementation is likely to be particularly effective in the presence of such MTHFR polymorphisms; this line of reasoning was supported by improved cognitive performance in mice lacking one or both murine MTHFR alleles (Chan et al., (2007) in press). The findings of the study described herein highlight a potential link between nutritional and genetic risk factors for AD: dietary folate and vitamin E deficiency potentiated ApoE deficiency, which increased PS-1, which in turn increased gamma-secretase and increased Abeta.

Equivalents

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

methionine in an amount sufficient to cause a statistically significant improvement in the subject's performance on one or more standard cognitive tests, wherein the formulation consists essentially of 400 μg folate, 6 μg vitamin B12, 30 IU vitamin E, 400 mg S-adenosyl methionine, 600 mg N-acetyl cysteine, and 500 mg acetyl-L-carnitine.

What is claimed:

1. A method of improving cognitive performance in a human subject, comprising administering to the subject a formulation comprising folate, vitamin E, vitamin B12, N-acetyl cysteine, acetyl-L-carnitine, and S-adenosyl methionine in an amount sufficient to cause a statistically significant improvement in the subject's performance on one or more standard cognitive tests, wherein the formulation consists essentially of 400 μg folate, 6 μg vitamin B12, 30 IU vitamin E, 400 mg S-adenosyl methionine, 600 mg N-acetyl cysteine, and 500 mg acetyl-L-carnitine.

2. The method of claim 1, wherein the subject is a normal adult.

3. The method of claim 2, wherein the standard cognitive test is selected from the group consisting of Trail Making Test A, Trail Making Test B, and combinations thereof.

4. The method of claim 1, wherein the subject suffers from a neurodegenerative disorder.

5. The method of claim 4, wherein the neurodegenerative disorder is selected from the group consisting of Alzheimer's disease, Parkinson's disease, or amyotrophic lateral sclerosis (ALS).

6. The method of claim 4, wherein the neurodegenerative disorder is early stage Alzheimer's disease.

7. The method of claim 4, wherein the neurodegenerative disorder is mid/late stage Alzheimer's disease.

8. The method of claim 4, wherein the standard cognitive test is selected from the group consisting of Dementia Rating Scale 2 (DRS-2), Clox 1, Clox 2, and combinations thereof.

9. The method of claim 1, wherein the formulation is administered orally.

10. The method of claim 1, wherein the formulation further comprises a pharmaceutically acceptable carrier.

11. The method of claim 1, wherein the formulation is administered in combination with one or more additional nutriceutical or pharmaceutical compositions selected from the group consisting of donepezil, galantamine, rivastigmine, memantine, haloperidol, risperidone, olanzapine, clozapine, ziprasidone, quetiapine, fluoxetine hydrochloride, paroxetine, citalopram, sertraline hydrochloride, nortriptyline, alprazolam, lorazepam, oxazepam, and buspirone.

12. The method of claim 1, wherein the formulation is packaged with the folate, vitamin E, vitamin B12, N-acetyl cysteine, acetyl-L-carnitine and S-adenosyl methionine in one or more combination or individual dosage forms.

13. The method of claim 1, wherein the formulation is administered twice daily.

14. The method of claim 1, wherein the subject is at risk of developing Alzheimer's Disease.

15. The method of claim 14, wherein the administration delays the onset of Alzheimer's Disease in the subject.

16. The method of claim 1, wherein the subject lacks dementia.

17. The method of any one of claims 6, 7, 14, and 16, wherein the administration delays cognitive decline in the subject.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
acggtttcca acatccatcg                                              20

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
gatgacaggg actgttgagc aa                                           22

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
accacagtcc atgccatcac                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tccaccaccc tgttgctgta                                              20

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Gly Val Val Ile Ala Thr Val Ile Val
1               5
```